United States Patent
Gendelman et al.

(10) Patent No.: US 11,209,426 B2
(45) Date of Patent: Dec. 28, 2021

(54) METHOD FOR DIAGNOSING AND TREATING PARKINSON'S DISEASE VIA MEASURMENT OF EFFECTOR MEMORY T-CELLS

(71) Applicant: Board of the Regents of the University of Nebraska, Lincoln, NE (US)

(72) Inventors: Howard E. Gendelman, Omaha, NE (US); R. Lee Mosley, Omaha, NE (US); Jessica A. Saunders, Stanford, CA (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 14/357,682

(22) PCT Filed: Dec. 7, 2012

(86) PCT No.: PCT/US2012/068423
§ 371 (c)(1),
(2) Date: May 12, 2014

(87) PCT Pub. No.: WO2013/086304
PCT Pub. Date: Jun. 13, 2013

(65) Prior Publication Data
US 2014/0349877 A1    Nov. 27, 2014

Related U.S. Application Data

(60) Provisional application No. 61/617,759, filed on Mar. 30, 2012, provisional application No. 61/568,015, filed on Dec. 7, 2011.

(51) Int. Cl.
*G01N 33/543* (2006.01)
*G01N 33/68* (2006.01)
*G01N 33/53* (2006.01)

(52) U.S. Cl.
CPC ....... *G01N 33/54306* (2013.01); *G01N 33/53* (2013.01); *G01N 33/6896* (2013.01); *G01N 2800/2835* (2013.01)

(58) Field of Classification Search
CPC ......... G01N 33/54306; G01N 33/6896; G01N 33/53; G01N 2800/2835
See application file for complete search history.

(56) References Cited

U.S. PATENT DOCUMENTS

| | | | |
|---|---|---|---|
| 6,653,325 B2 * | 11/2003 | Svensson | A61K 31/445 514/317 |
| 2009/0215636 A1 | 8/2009 | Krizman et al. | |
| 2010/0233733 A1 | 9/2010 | Fantl et al. | |

FOREIGN PATENT DOCUMENTS

WO    2005103721    3/2005

OTHER PUBLICATIONS

Woerner et al (Cancer Research (2005) vol. 65, pp. 11392-11399) teaches a phosphor-CXCR4 specific antibody.*
Shimoji et al. CXCR4 and CXCL12 expression is increased in the nigro-striatal system of Parkinson's disease. Neurotox Res. Oct. 2009;16(3):318-28. Epub Jun. 24, 2009.*
Baba et al. Alterations of T-lymphocyte populations in Parkinson disease. Parkinsonism Relat Disord. Dec. 2005;11(8):493-8. Epub Sep. 9, 2005.*
Seddiki et al. Expression of interleukin (IL)-2 and IL-7 receptors discriminates between human regulatory and activated T cells. J Exp Med. Jul. 10, 2006;203(7):1693-700. Epub Jul. 3, 2006.*
Reynolds et al., Regulatory T cells attenuate Th17 cell-mediated nigrostriatal dopamanergic neurodegeneration in a model of Parkinson's disease, 2010, J. Immunol. 2261-2271, 184.
Bas et al., Lymphocyte populations in Parkinson's disease and in rat models of parkinsonism, J Neuroimmunol., 2001,146-5, 113(1).
Calopa et al., Apoptosis of peripheral blood lymphocytes in Parkinson patients, Neurobiol Dis., 2010,1-7, 38(1).
Lebouvier et al., Colonic biopsies to assess the neuropathology of Parkinson's disease and its relationship with symptoms, PLoS One, 2010, e12728, 5(9).
Forsyth et al., Increased intestinal permeability correlates with sigmoid mucosa alpha-synuclein staining and endotoxin exposure markers in early Parkinson's disease, PLoS One, 2011, e28032, 6(12).
Mosley et al., Inflammation and adaptive immunity in Parkinson's disease, 2012, Cold Spring Harbor Perspectives in Medicine, Cold Spring Harbor Laboratory Press, pp. 1-17, 2(a009381).
Hutter-Saunders et al., Pathways towards an effective immunotherapy for Parkinson's disease, Expert Rev Neurother., 2011, 1703-15, 11(12).
Hutter-Saunders et al., CD4+ Regulatory and Effector/Memory T Cell Subsets Profile Motor Dysfunction in Parkinson's Disease, J Neuroimmune Pharmacol., 2012, 927-38, 7(4).
Reynolds et al., Nitrated alpha-synuclein-induced alterations in microglial immunity are regulated by CD4+ T cells subsets, J. of Immuno., 2009, 4137-4149, 182.
Fiszer, et al., "Parkinson's disease and immunological abnormalities: increase of HLA-DR expression on monocytes in cerebrospinal fluid and of CD45RO+ T cells in peripheral blood" Acta Neurol Scand. (1994) 90(3):160-6.

* cited by examiner

*Primary Examiner* — Gregory S Emch
(74) *Attorney, Agent, or Firm* — Robert C. Netter, Jr.; Dann, Dorfman, Herrell & Skillman

(57) ABSTRACT

Methods and compositions for detecting and diagnosing Parkinson's disease are disclosed.

17 Claims, 13 Drawing Sheets

|  | Cohort A | | | | | | | Cohort B | | | | | | |
|---|---|---|---|---|---|---|---|---|---|---|---|---|---|---|
|  | Caregivers | | PD patients | | | | | Caregivers | | PD patients | | | | |
|  | n | Mean ± SD | n | Mean ± SD | p value | | | n | Mean ± SD | n | Mean ± SD | p value | | |
| Age (yrs.) | 28 | 61 ± 10 | 38 | 64 ± 8 | 0.14 | | | 57 | 64 ± 11 | 72 | 67 ± 10 | 0.12 | | |
| Disease duration (yrs.) | - | - | 37 | 4.5 ± 2.5 | NA | | | - | - | 72 | 4 ± 2.5 | NA | | |
| H&Y stage | - | - | 34 | 2 ± 0.5 | NA | | | - | - | 71 | 2 ± 1 | NA | | |
| UPDRS-III score | - | - | 36 | 26 ± 10 | NA | | | - | - | 70 | 24 ± 11 | NA | | |
|  | Caregivers | | PD patients | | | | | Caregivers | | PD patients | | | | |
|  | n | Percent | n | Percent | p value | | | n | Percent | n | Percent | p value | | |
| Gender, male | 30 | 27 | 41 | 78 | <0.0001 | | | 65 | 23 | 72 | 75 | <0.0001 | | |
| Race, Caucasian | 30 | 100 | 41 | 90 | NA | | | 65 | 98 | 72 | 99 | NA | | |
| Job with pesticides | 30 | 13 | 41 | 25 | >0.05 | | | 65 | 8 | 71 | 25 | 0.006 | | |
| Exposure to pesticides | 30 | 47 | 40 | 78 | 0.04 | | | 59 | 39 | 70 | 70 | 0.05 | | |
| Job with chemical solvents | 30 | 10 | 41 | 37 | 0.024 | | | 63 | 10 | 71 | 27 | 0.002 | | |
| Job with heavy metals | 30 | 7 | 41 | 17 | >0.05 | | | 63 | 3 | 71 | 13 | 0.04 | | |
| Job with other chemical fumes | 29 | 4 | 40 | 13 | >0.05 | | | 63 | 14 | 71 | 31 | 0.01 | | |

Figure 8

| Population | Population Subset | Caregivers | | | | | PD patients | | | | | p values | |
|---|---|---|---|---|---|---|---|---|---|---|---|---|---|
| | | N | Mean ± SEM (%) | Median (%) | Range (%) | | N | Mean ± SEM (%) | Median (%) | Range (%) | | Mann-Whitney | Benjamini-Hochberg |
| CD4+ T cells | CD45RO+ | 23 | 65.0 ± 2.31 | 66.2 | 41.0-80.2 | | 29 | 74.7 ± 1.8 | 75.3 | 48.8-91.0 | | 0.002 | 0.008 |
| | CD45RA+ | 23 | 25.5 ± 2.1 | 24.4 | 9.8-47.6 | | 29 | 16.9 ± 1.6 | 16.3 | 4.8-36.8 | | 0.002 | 0.008 |
| | FAS+ | 23 | 58.4 ± 2.8 | 52.8 | 37.9-79.7 | | 30 | 69.6 ± 2.3 | 70.0 | 39.1-88.4 | | 0.005 | 0.012 |
| | CD31+ | 23 | 28.2 ± 1.9 | 26.6 | 11.1-43.0 | | 30 | 22.9 ± 1.8 | 20.8 | 8.9-42.7 | | 0.025 | 0.035 |
| | Integrin β7+ | 23 | 36.6 ± 2.7 | 36.4 | 17.7-60.2 | | 30 | 29.8 ± 1.4 | 30.0 | 15.9-5.0 | | 0.025 | 0.035 |
| | CD25+ | 27 | 9.1 ± 0.3 | 8.8 | 6.1-13.5 | | 33 | 9.7 ± 0.4 | 9.6 | 6.9-16.5 | | 0.28 | 0.33 |
| | CD127+ | 27 | 59.1 ± 1.88 | 60.4 | 36.8-75.8 | | 33 | 61.5 ± 1.5 | 64.0 | 42.7-76.3 | | 0.36 | 0.36 |
| CD4+CD25+ CD127+ Teff | CD45RO+ | 23 | 87.1 ± 1.3 | 89.8 | 72.3-96.6 | | 28 | 90.4 ± 1.2 | 91.8 | 70.1-97.1 | | 0.03 | 0.07 |
| | CD45RA+ | 23 | 4.0 ± 0.6 | 3.1 | 0.7-10.3 | | 28 | 2.9 ± 0.8 | 1.8 | 0.5-17.7 | | 0.02 | 0.07 |
| | FAS+ | 24 | 90.6 ± 2.1 | 94.4 | 48.9-97.6 | | 31 | 94.1 ± 1.1 | 95.9 | 68.8-99.6 | | 0.08 | 0.10 |
| | CD31+ | 25 | 24.0 ± 1.5 | 23.3 | 9.2-36.4 | | 30 | 20.3 ± 1.8 | 18.6 | 7.0-38.9 | | 0.12 | 0.12 |
| | Integrin β7+ | 25 | 21.4 ± 1.6 | 20.5 | 6.3-39.8 | | 31 | 18.3 ± 1.7 | 16.6 | 7.0-59.7 | | 0.06 | 0.08 |
| CD4+CD25+ CD127- Treg | CD45RO+ | 23 | 71.5 ± 1.1 | 82.6 | 71.5-92.6 | | 28 | 86.4 ± 1.0 | 87.8 | 73.9-93.3 | | 0.012 | 0.07 |
| | CD45RO- | 23 | 9.5 ± 1.0 | 9.2 | 1.8-21.4 | | 28 | 7.1 ± 0.9 | 5.8 | 1.5-20.4 | | 0.04 | 0.07 |
| | FAS+ | 24 | 51.4 ± 83.5 | 94.3 | 82.5-2.0 | | 31 | 71.3 ± 88.5 | 96.6 | 86.9-1.3 | | 0.04 | 0.07 |
| | CD31+ | 25 | 8.7 ± 22.4 | 41.4 | 24.9-1.8 | | 30 | 6.6 ± 18.3 | 41.3 | 20.8-1.9 | | 0.10 | 0.11 |
| | Integrin β7+ | 25 | 10 ± 14.2 | 25.5 | 15.6-0.9 | | 31 | 8.3 ± 12.3 | 21.9 | 13.0-0.6 | | 0.03 | 0.07 |

Figure 9

|  | Caregivers | | | | PD patients | | | | p values |
| --- | --- | --- | --- | --- | --- | --- | --- | --- | --- |
|  | n | Mean ± SEM | Median | Range | n | Mean ± SEM | Median | Range | Mann–Whitney |
| Hgb (g/dL) | 47 | 13.7±0.2 | 13.8 | 11.1–17.3 | 59 | 14.1±0.2 | 14 | 11.6–17.3 | 0.08 |
| WBCx 10³/µL | 47 | 6.4±0.3 | 6 | 3.6–11.4 | 59 | 6.2±0.2 | 6 | 3.3–12.1 | 0.57 |
| Neutrophil (%) | 36 | 57.5±1.8 | 60 | 27–77 | 43 | 63.6±1.5 | 64 | 43–86 | 0.01 |
| Lymphocyte (%) | 36 | 29.7±1.6 | 28.5 | 10–59 | 43 | 24.1±1.2 | 23 | 7–38 | 0.01 |
| Monocyte (%) | 36 | 8.6±0.4 | 8 | 5–14 | 43 | 8.4±0.3 | 8 | 4–13 | 0.75 |
| Eosinophil (%) | 36 | 3.7±0.3 | 3 | 0–9 | 43 | 3.4±0.5 | 3 | 0–13 | 0.70 |
| Basophil (%) | 36 | 0.6±0.1 | 1 | 0–1 | 43 | 0.4±0.1 | 0 | 0–2 | 0.12 |
| Absolute Lymphocyte count/µL | 36 | 1829.3±174 | 1537.5 | 737–6726 | 43 | 1434.6±89.4 | 1340 | 570–3335 | 0.04 |
| ᵃAbsolute CD4+ count/µL | 36 | 801.3±115.4 | 591.5 | 334.3–4424 | 43 | 541.3±37.9 | 469.4 | 207–1231 | 0.008 |

Figure 10

| Population | Population Subset | Caregivers | | | | PD patients | | | | p-values | |
|---|---|---|---|---|---|---|---|---|---|---|---|
| | | n | Mean ± SEM (%) | Median (%) | Range (%) | n | Mean ± SEM (%) | Median (%) | Range (%) | Mann-Whitney | Benjamini-Hochberg |
| CD4+ T cells | CD45RO+ | 62 | 64.4±1.5 | 65.2 | 37.6–93.4 | 71 | 69.6±1.5 | 69.7 | 22.4–91.4 | 0.009 | 0.028 |
| | CD45RA+ | 62 | 27.5±1.4 | 27.8 | 3.0–54.0 | 71 | 22.4±1.5 | 21.4 | 2.1–72.8 | 0.004 | 0.028 |
| | FAS+ | 65 | 60.0±1.8 | 61.2 | 27.7–96.1 | 72 | 67.0±1.7 | 67.6 | 22.4–93.3 | 0.006 | 0.028 |
| | CD31+ | 65 | 28.8±0.9 | 28.1 | 14.7–47.3 | 72 | 25.3±0.9 | 25.6 | 10.6–41.2 | 0.014 | 0.031 |
| | Integrin α4β7+ | 53 | 37.6±1.5 | 36.6 | 20.8–60.0 | 58 | 31.8±1.3 | 33.3 | 12.0–55.6 | 0.021 | 0.034 |
| | Integrin α4β1+ | 41 | 52.5±1.5 | 50.7 | 38.2–78.2 | 47 | 55.6±1.6 | 54.5 | 34.4–82.0 | 0.08 | 0.10 |
| | CD25+ | 64 | 13.2±0.4 | 13.0 | 6.8–21.1 | 71 | 13.7±0.4 | 13.3 | 7.1–20.8 | 0.48 | 0.54 |
| | CD127+ | 64 | 63.7±0.8 | 64.0 | 44.0–77.0 | 71 | 64.2±0.8 | 64.7 | 44.9–79.6 | 0.66 | 0.66 |
| CD4+CD25+ CD127+ Teff | CD45RO+ | 60 | 88.1±0.8 | 89.9 | 69.4–97.6 | 70 | 89.2±0.9 | 91.6 | 57.0–98.4 | 0.07 | 0.08 |
| | CD45RA+ | 60 | 5.2±0.6 | 3.7 | 0.2–20.4 | 70 | 4.6±0.7 | 2.8 | 0.2–33.9 | 0.05 | 0.06 |
| | FAS+ | 63 | 89.9±1.3 | 92.2 | 35.4–99.3 | 71 | 92.7±0.8 | 95.0 | 60.9–98.8 | 0.04 | 0.06 |

Figure 11

METHOD FOR DIAGNOSING AND TREATING PARKINSON'S DISEASE VIA MEASURMENT OF EFFECTOR MEMORY T-CELLS

This application is a § 371 application of PCT/US2012/068423, filed Dec. 7, 2012, which claims priority under 35 U.S.C. § 119(e) to U.S. Provisional Patent Application No. 61/617,759, filed on Mar. 30, 2012 and to U.S. Provisional Patent Application No. 61/568,015, filed on Dec. 7, 2011. The foregoing applications are incorporated by reference herein.

This invention was made with government support under P01 DA028555, R01 NS034239, R37 NS36126, P01 NS31492, P20 RR15635, P01 MH64570, R01 NS070190, and P01 NS43985 awarded by the National Institutes of Health. The government has certain rights in the invention.

FIELD OF THE INVENTION

The present invention relates to the fields of central nervous system disorders. More specifically, the invention provides compositions and methods for the diagnosis of central nervous disorders, particularly Parkinson's disease.

BACKGROUND OF THE INVENTION

Several publications and patent documents are cited throughout the specification in order to describe the state of the art to which this invention pertains. Each of these citations is incorporated herein by reference as though set forth in full.

Parkinson's disease (PD) is a common progressive neurodegenerative disease clinically characterized by resting tremor, muscle rigidity, bradykinesia, and postural instability (Dauer et al. (2003) Neuron 39:889-909). PD is sporadic and of unknown cause although host genetics, environmental cues, aging, impaired energy metabolism and oxidative stress are linked to disease onset and progression (Klockgether, T. (2004) Cell Tissue Res., 318:115-120). Pathologically, PD is characterized by degeneration of dopaminergic cell bodies in the substantia nigra pars compacta (SNpc) and their associated caudate projections (Dauer et al. (2003) Neuron 39:889-909). Nonetheless, the pathological hallmark of PD is cytoplasmic inclusions of fibrillar, misfolded proteins called Lewy bodies composed principally of alpha-synuclein (α-Syn) (Spillantini et al. (1997) Nature, 388: 839-840).

α-Syn is a 140-amino acid (aa), natively unfolded, soluble protein that is localized in the pre-synaptic terminals of neurons of the central nervous system (CNS), where it interacts with and may regulate synaptic vesicles (Spillantini et al. (1997) Nature 388: 839-840; Sidhu et al. (2004) FASEB J., 18:637-647; Paxinou et al. (2001) J. Neurosci., 21:8053-8061; Weinreb et al. (1996) Biochemistry 35:13709-13715; Eliezer et al. (2001) J. Mol. Biol., 307: 1061-1073; Uversky et al. (2000) Proteins 41:415-427). Three missense mutations (A53T, A30P and E46K) in the gene encoding α-Syn are linked to dominantly inherited PD (Kruger et al. (1998) Nat. Genet., 18:106-108; Polymeropoulos, et al. (1997) Science, 276:2045-2047; Zarranz et al. (2004) Ann. Neurol., 55:164-173). Moreover, multiplication of the wild-type (WT) gene has also been linked to PD, suggesting that the level of α-Syn is an important pathogenic factor (Chartier-Harlin et al. (2004) Lancet 364:1167-1169; Singleton et al. (2003) Science 302:841). Such familial cases are rare and in sporadic PD, there is no genetic aberration of α-Syn. However, it has been proposed that post-translational modifications such as nitration enhances WT α-Syn propensity to aggregate (Hodara et al. (2004) J. Biol. Chem., 279:47746-47753; Uversky et al. (2001) J. Biol. Chem., 276:10737-10744; Uversky et al. (2005) Brain Res. Mol. Brain. Res., 134:84-102; Yamin et al. (2003) FEBS Lett., 542:147-152). Oxidized and aggregated α-Syn, when released from dying neurons, may stimulate scavenger receptors on microglia resulting in their sustained activation and dopaminergic neurodegeneration (Wersinger et al. (2006) Curr. Med. Chem., 13: 591-602; Zhang et al. (2005) FASEB J., 19:533-542; Croisier et al. (2005) J. Neuroinflammation 2:14). Moreover, activated microglia generate nitric oxide and superoxide that rapidly react to form peroxynitrite which can then traverse cell membranes resulting in 3-nitrotyrosine (NT) formation, DNA damage, mitochondrial inhibition, or lipid peroxidation (Dringen, R. (2005) Antioxid. Redox. Signal 7:1223-1233; Ischiropoulos, et al. (2003) J. Clin. Invest., 111:163-169).

Despite the above understanding of PD, there are no methods currently available to detect PD at an early stage. The ability to detect PD at an early stage would increase the ability to treat the disease as well as identify specific treatments for treating specific patient populations.

SUMMARY OF THE INVENTION

In accordance with the instant invention, methods of detecting or diagnosing a neurodegenerative disease (e.g., Parkinson's disease) in a subject are provided. In a particular embodiment, the method comprises detecting the increase or predominance of effector memory T cells in the subject. In a particular embodiment, the method comprises detecting in a biological sample obtained from the subject at least one marker (protein or encoding nucleic acid) from the C—X—C chemokine receptor type 4 (CXCR-4) or phosphatidylinositol 3-kinase regulatory subunit 1 (alpha) (PIK3R1) signaling pathways, wherein a modulation in the amount of the marker compared to healthy individuals is indicative of Parkinson's disease. In a particular embodiment, the marker is selected from the group consisting of PIK3R1, CXCR4, integrin alpha-V (ITGAV), integrin alpha-E (ITGAE), integrin beta-7 (ITGB7), integrin alpha-4 (ITGA4), cluster of differentiation (CD) 31 (CD31), secreted phosphoprotein 1 (SPP1), CD45, forkhead box P3 (FoxP3), fibronectin 1 (FN1), CD27, CD4, CD127, CD25, and FAS. In a particular embodiment, the marker is selected from the group consisting of CD4, CD127, CD25, CD27, CD45RA, CD45RO, CD31, FAS, integrin beta-7, and integrin alpha-4. In another embodiment, the marker is selected from the group consisting of CD45RA, CD45RO, CD31, FAS, integrin beta-7, and integrin alpha-4. The method may further comprise characterizing the severity of the Parkinson's disease (e.g., in terms of a UPDRS-III score) in the subject by correlating (either directly or inversely) the amount the marker to the severity of Parkinson's disease in controls. The markers may be detected with an antibody immunologically specific for the marker. The markers may also be detected with a nucleic acid molecule (e.g., probes or primers) that specifically hybridizes with the nucleic acid molecule encoding the marker.

In accordance with another aspect of the instant invention, compositions comprising at least one agent for detecting at least one marker (e.g., protein or nucleic acid) of the instant invention and a carrier are provided. In a particular embodiment, the marker is selected from the group consisting of CD4, CD127, CD25, CD27, CD45RA, CD45RO, CD31, FAS, integrin beta-7, and integrin alpha-4. In another embodiment, the marker is selected from the group consisting of CD45RA, CD45RO, CD31, FAS, integrin beta-7, and integrin alpha-4. The detection agents (e.g., antibodies, probes, etc.) may be attached to a solid support (e.g., as in an array). Kits comprising at least one composition and/or array are also encompassed by the instant invention.

BRIEF DESCRIPTION OF THE DRAWINGS

FIG. 1A provides representative flow cytometric scatter plots used for data collection. The CD4+ T cell population was identified by high expression of CD4 and low side scatter (left panel). Regulatory T cells (Treg) and effector T cells (Teff) were identified within the CD4+ T cell population as CD25+CD127− and CD25+CD127+, respectively (right panel). FIG. 1B provides a graph of the percentage of CD4+ lymphocytes for Cohort B. CD4+ data are expressed as means±standard error of the mean (SEM), and significant differences between CD4+ T cell means were determined by Mann-Whitney test for 63 caregivers and 71 PD patients where $*p \leq 0.05$.

FIG. 3A provides a scatter plot of the percentages of FAS+ CD4+ T cells against the percentages of CD45RO+ CD4+ T cells for Cohort B (Pearson r=0.87, p<0.001). FIG. 3B provides a scatter plot of the percentages of CD31+ CD4+ T cells against the percentages of CD45RO+ CD4+ T cells for Cohort B (Pearson r=0.33, p<0.0001). FIG. 3C provides a scatter plot of the percentages of FAS+ CD4+ T cells against the percentages of CD31+ CD4+ T cells (Pearson r=0.29, p<0.001). Data are displayed as the percentages of CD4+ T cells, and correlations were determined using Pearson product-moment correlation coefficients for PD patients and caregivers combined (n=136) from Cohort B. Best-fit lines were determined by linear regression.

FIG. 4A provides a scatter plot of the percentages of CD45RO+ CD4+ T cells against UPDRS-III score (Pearson r=0.35, p=0.003, n=69). FIG. 4B provides a scatter plot of the percentages of FAS+ CD4+ T cells against UPDRS-III score (Pearson r=0.24, p=0.043, n=70). FIG. 4C provides a scatter plot of the percentages of CD31+ CD4+ T cells against UPDRS-III (Pearson r=−0.49, p<0.001, n=70). FIG. 4D provides a scatter plot of the percentages of integrin α4β7+ CD4+ T cells against UPDRS-III (Pearson r=−0.29, p=0.02, n=58). FIG. 4E provides a scatter plot of the percentages of CD31+ Teff against UPDRS-III score (Pearson r=−0.47, p<0.0001, n=69). FIG. 4F provides a scatter plot of the percentages of α4β7+ Teff against UPDRS-III score (Pearson r=−0.32, p=0.017, n=57). Data are displayed as the percentages of CD4+ T cells (FIG. 4A-4D) or CD25+ CD127+CD4+ Teff (4E and 4F) and correlations were determined using Pearson product-moment correlation coefficients. Best-fit lines were determined by linear regression.

FIG. 6B shows the inhibition of proliferation of Tresp by Treg at ratios of 1:1 (n=28), 1:0.5 (n=26), 1:0.25 (n=28) and 1:0.125 (n=25) of Tresp to Treg, demonstrating that Treg from PD patients had significant decreased inhibitory capacity at the 1:0.125 dilution (p=0.006). FIG. 6C shows CD25 expression was not altered at any dilution. FIG. 6D shows that the percentage of proliferating Teff did not differ (p<0.05) for PD patients (n=34) compared to caregivers (n=32). FIG. 6E shows that the percentage of proliferating nT did not differ (p<0.05) for PD patients (n=16) compared to caregivers (n=15). Data are expressed as the percentage of proliferating cells out of all CFSE+ events. Significant differences among groups were determined by Kruskal-Wallis nonparametric ANOVA, and pair-wise comparisons determined by Dunn's multiple comparison's post-hoc analysis (FIGS. 6B, 6C) or by Mann-Whitney test (FIGS. 6D, 6E).

FIG. 8 provides a table of the descriptive data of Cohorts A and B.

FIG. 9 provides a table of the phenotypic analysis of CD4+ T cells and CD4+ T cell subsets from PD patients compared to caregivers in Cohort A.

FIG. 10 provides a table of the complete blood counts and differential blood cell counts from PD patients compared to caregiver controls of Cohort B. Absolute CD4+ T cell count was calculated using the percentage of CD4+ T cells determined by flow cytometric analysis with the absolute lymphocyte count determined by differential blood cell count.

FIG. 11 provides a table of the phenotypic analysis of CD4+ T cells and CD4+ T cell subsets from PD patients compared to caregivers in Cohort B.

DETAILED DESCRIPTION OF THE INVENTION

Figure 1:
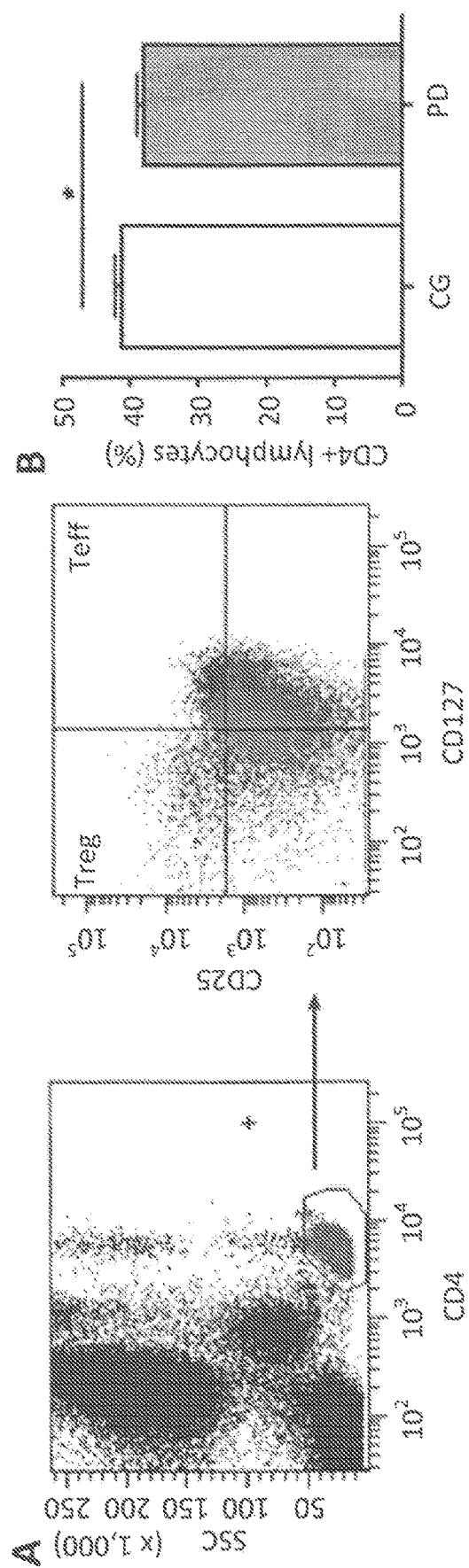
FIG. 1 shows the gating strategy for flow cytometric analysis of PBMC and CD4+ T cell and Teff frequency.

Parkinson's disease (PD) is the most common neurodegenerative motor disorder (Hirtz et al. (2007) Neurology 68:326-337). Loss of dopaminergic neurons and dopamine characterize the progressive loss of motor function and disease severity. Mounting experimental and clinical evidence has linked neuroinflammation to the pathobiology of PD (Mosley et al. (2012) Cold Spring Harb. Perspect. Med., 2:a009381) whereby activated microglia and astrocytes comprise integral components of PD pathology (Pouplard et al. (1984) Adv. Neurol., 40:307-313; Barker et al. (1988) Int. J. Neurosci., 43:1-7; McGeer et al. (2008) Mov. Disord., 23:474-483; McGeer et al. (1988) Neurology 38:1285-1291). Moreover, CD4+ and CD8+ T cells are found in close proximity to dopaminergic neurons in both PD brains (Brochard et al. (2009) J. Clin. Invest., 119:182-192) and in 1-methyl-4-phenyl-1,2,3,6-tetrahydropyridine (MPTP)-treated mice (Kurkowska-Jastrzebska et al. (1999) Exp. Neurol., 156:50-61; Benner et al. (2008) PLoS One 3:e1376). In peripheral blood, decreased numbers of total lymphocytes are linked to decreased CD4+ T cell counts and percentages (Hoffman et al. (1978) N. Engl. J. Med., 299: 680-685; Bas et al. (2001) J. Neuroimmunol., 113:146-152; Hisanaga et al. (2001) Arch. Neurol., 58:1580-1583; Baba et al. (2005) Parkinsonism Relat. Disord., 11:493-498; Calopa et al. (2010) Neurobiol. Dis., 38:1-7), which parallel reduced naïve and increased memory CD4+ T cells (Fiszer et al. (1994) Acta Neurol. Scand., 90:160-166; Bas et al. (2001) J. Neuroimmunol., 113:146-152; Calopa et al. (2010) Neurobiol. Dis., 38:1-7), increased $CD4^{bright}CD8^{dull}$ T cells expressing CD45RO and FAS (Hisanaga et al. (2001) Arch. Neurol., 58:1580-1583), and increased CD4+ CD25+ Tcells (Bas et al. (2001) J. Neuroimmunol., 113:146-152; Baba et al. (2005) Parkinsonism Relat. Disord., 11:493-498; Rosenkranz et al. (2007) J. Neuroimmunol., 188:117-127; Calopa et al. (2010) Neurobiol. Dis., 38:1-7). Although the cause and effects of such changes in T cell pools have not been precisely delineated, it is possible that T cells influence neurodegeneration. In support of this idea, modified forms of alpha synuclein (α-Syn) are present in the periphery (Beach et al. (2010) Acta Neuropathol., 119:689-702) and may act as neoantigens to break immune tolerance, and as such induce effector T cell (Teff) responses and subsequent neurotoxic reactions. Indeed, studies have demonstrated that induction of Teff speeds nigrostriatal degeneration following nitrated α-Syn immunization (Benner et al. (2008) PLoS One 3:e1376). More recent works show that such effects are mediated through Th17 cells. These cells serve to exacerbate neurodegeneration while regulatory T cells (Treg) elicit neuroprotective responses as demonstrated in MPTP-intoxicated mice (Reynolds et al. (2010) J. Immunol., 184:2261-2271). In addition, Treg function is diminished in α-Syn-immunized mice from which neurotoxic Th17 cells are isolated. Furthermore, decreased numbers of Treg are associated with increased rates of progression of amyotrophic lateral sclerosis (Beers et al. (2011) Brain 134:1293-1314; Rentzos et al. (2012) Acta Neurol. Scand., 125:260-264) another neurodegenerative movement disorder.

Based on these findings, it was hypothesized that alterations in the frequency, phenotype and function of CD4+ T cells and CD4+ T cell subsets exist in PD, and that altered immune status co-exists with disease severity. Herein, alterations in the peripheral CD4+ T cell, Treg, and Teff populations of PD patients compared with caregiver control subjects as well as with clinically-scored disease severity are described. More specifically, peripheral blood lymphocytes from two separate cohorts, a discovery cohort and a validation cohort, totaling 113 PD patients and 96 age- and environment-matched caregivers were examined by flow cytometric analysis and T cell proliferation assays. Phenotypic markers for effector/memory T (Tem) cells were associated with clinical outcomes of disease severity, but not disease duration. Indeed, increased effector/memory T cells (Tem), defined as CD45RO+ and FAS+ CD4+ T cells and decreased CD31+ and α4β7+ CD4+ T cells were associated with progressive Unified Parkinson's Disease Rating Scale (UPDRS) III scores. However, no associations were seen between immune biomarkers and increased age or disease duration. Further, impaired abilities of regulatory T cells (Treg) from PD patients to suppress effector T cell function were observed. These data demonstrate regulatory dysfunction with chronic activation of the adaptive immune system in PD which have profound influence on ongoing inflammatory-induced neuropathology and disease progression associated with PD. These data indicate that chronic immune stimulation, notably Tem activation and Treg dysfunction is linked to PD pathobiology and disease severity. The association of T cell phenotypes with motor symptoms provides fresh avenues for novel biomarkers and therapeutic designs.

In accordance with the instant invention, compositions and methods are provided for the detection and/or diagnosis of a neurodegenerative disease (e.g., Parkinson's disease). Examples of neurodegenerative disease include, without limitation, Alzheimer's disease, Parkinson's disease, Lewy Body disease, amyotrophic lateral sclerosis, prion disease, and Huntington's disease. While the instant invention may be used for other neurodegenerative diseases, the invention will generally be described for convenience in terms of Parkinson's disease.

The instant invention has demonstrated that the increase or predominance of effector memory T cells in the subject correlates with PD in the subject (e.g., its severity). In a particular embodiment, compositions and methods for the detection and/or diagnosis of Parkinson's disease comprise detecting, measuring, or quantitating an increase or predominance of effector memory T cells in the subject. In a particular embodiment, the compositions and methods of the instant invention use markers associated with increased effector/memory T cells. Indeed, as the severity of PD increases, the Tem cell phenotype predominates. In a particular embodiment, the markers of the instant invention comprise at least one, two, three, four, five, six, seven, eight, nine, ten, or more markers from a signaling pathway involving C—X—C chemokine receptor type 4 (CXCR-4) or phosphatidylinositol 3-kinase regulatory subunit 1 (alpha) (PIK3R1). Specific marker examples include, without limitation: PIK3R1, CXCR4, integrin alpha-V (ITGAV), integrin alpha-E (ITGAE), integrin beta-7 (ITGB7 (including integrin alpha 4 beta 7)), integrin alpha-4 (ITGA4), cluster of differentiation (CD) 31 (CD31; platelet endothelial cell adhesion molecule (PECAM-1)), secreted phosphoprotein 1 (SPP1), CD45 (CD45R and isoforms thereof including CD45RA and CD45RO; protein tyrosine phosphatase, receptor type C (PTPRC)), forkhead box P3 (FoxP3), fibronectin 1 (FN1), CD27, CD4, CD127, CD25, and FAS. In a particular embodiment, the markers of the instant invention comprise at least one, two, three, four, five, six, seven, eight, or more markers from the group of CD4, CD127, CD25, CD45RA, CD45RO, CD31, FAS, CD27, and integrin α4β7. In a particular embodiment, the markers of the instant invention comprise at least one, two, three, four, five or more markers from the group of CD45RA, CD45RO, CD31, FAS, and integrin α4β7 (e.g., ITGB7 and/or ITGA4). In a particular embodiment, the markers of the instant invention comprise at least one, two, three, four, or more markers from the group of CD45RO, CD31, FAS, and integrin α4β7 (e.g., ITGB7 and/or ITGA4).

In a particular embodiment of the invention, the markers are mammalian, particularly human. The nucleotide and amino acid sequence of the above markers are known by those of skill in the art and can be readily accessed from a variety of genomic databases such as GenBank. Examples of the human nucleotide and amino acid sequences of the above markers are provided:

1) PIK3R1: Gene ID: 5295; GenBank Accession Nos.: NM_001242466.1, NP_001229395.1, NM_181504.3, NP_852556.2, NM_181523.2, NP_852664.1, NM_181524.1, and NP_852665.1;

2) CXCR4: Gene ID: 7852; GenBank Accession Nos.: NM_001008540.1, NP_001008540.1, NM_003467.2, and NP_003458.1;

3) ITGAV: Gene ID: 3685; GenBank Accession Nos.: NM_001144999.1, NP_001138471.1, NM_001145000.1, NP_001138472.1, NM_002210.3, and NP_002201.1;

4) ITGAE: Gene ID: 3682; GenBank Accession Nos.: NM_002208.4 and NP_002199.3;

5) ITGB7: Gene ID: 3695; GenBank Accession Nos.: NM_000889.1 and NP_000880.1;

6) ITGA4: Gene ID: 3676; GenBank Accession Nos.: NM_000885.4 and NP_000876.3;

7) CD31: Gene ID: 5175; GenBank Accession Nos.: NM_000442.4 and NP_000433.4;

8) SPP1: Gene ID: 6696; GenBank Accession Nos.: NM_000582.2, NP_000573.1, NM_001040058.1, NP_001035147.1, NM_001040060.1, NP_001035149.1, NM_001251829.1, NP_001238758.1, NM_001251830.1, and NP_001238759.1;

9) CD45: Gene ID: 5788; GenBank Accession Nos.: NM_001267798.1, NP_001254727.1, NM_002838.4, NP_002829.3, NM_080921.3, and NP_563578.2;

10) FOXP3: Gene ID: 50943; GenBank Accession Nos.: NM_001114377.1, NP_001107849.1, NM_014009.3, and NP_054728.2;

11) FN1: Gene ID: 2335; GenBank Accession Nos.: NM_002026.2, NP_002017.1, NM_054034.2, NP_473375.2, NM_212474.1, NP_997639.1, NM_212476.1, NP_997641.1, NM_212478.1, NP_997643.1, NM_212482.1, and NP_997647.1;

12) CD27: Gene ID: 939; GenBank Accession Nos.: NM_001242.4 and NP_001233.1;

13) CD4: Gene ID: 920; GenBank Accession Nos.: NM_000616.4, NP_000607.1, NM_001195014.2, NP_001181943.1, NM_001195015.2, NP_001181944.1, NM_001195016.2, NP_001181945.1, NM_001195017.2, and NP_001181946.1;

14) CD127: Gene ID: 3575; GenBank Accession Nos.: NM_014034.2, NM_002185, NP_002176.2, and NM_002185.3;

15) CD25: Gene ID: 3559; GenBank Accession Nos.: NG_007403.1, NM_000417, NP_000408.1, and NM_000417.2; and 16) FAS: Gene ID: 355; GenBank Accession Nos.: NM_000043.4, NP_000034.1, NM_152871.2, NP_690610.1, NM_152872.2, and NP_690611.1.

In a particular embodiment, the methods of the instant invention comprise detecting and/or measuring in a biological sample (e.g., blood, PBMCs, lymphocytes, T cells, CD4+ T cells, etc.) obtained from a subject, at least one of the above markers. The method may comprise detecting and/or measuring the amount of at least one, two, three, four, five, six, seven, eight, nine, ten, or more of the above markers. The amount of marker can be quantitated or assessed as a percentage or ratio of cells expressing the marker. The amount of marker detected or measured may be compared to a healthy control and/or PD controls to determine the presence and/or severity of PD in the test subject. For example, a modulation in the amount of marker detected or measured compared to a healthy control is indicative of the presence and/or severity of PD. The amount of marker detected or measured may be correlated with several (e.g., at least 2 or 3) standards of varying PD severity (e.g., different ranges of UPDRS-III score) to determine the severity of PD in the test subject. In a particular embodiment, the severity of PD is provided in terms of UPDRS-III scores. For example, with regard to the above markers, as the severity of PD increases (as UPDRS-III scores increase), CD45RA decreases, CD45RO increases, integrin β7 or α4 (e.g., α4β7) decreases, CD27 decreases, CD31 decreases, and FAS increases.

The methods may further comprise administering a therapeutic regimen to the subject upon diagnosis of PD. For example, the subject can be administered at least one of: a dopamine replacement therapy (e.g., L-DOPA (levopoda), L-DOPA with carbidopa; dopamine agonists; MOA-B inhibitors), a PD vaccine (e.g., U.S. patent application Ser. No. 12/500,414), deep brain stimulation, or adjuvant factors (e.g., granulocyte/macrophage-colony stimulating factor (GM-CSF)) that augment the immune response.

The markers of the instant invention may be detected and/or quantitated by any known method. Protein markers and/or nucleic acid molecules encoding the markers may be detected. For example, protein markers of the instant invention can be detected (e.g., via Western blot, flow cytometry (e.g., FACS), ELISA, etc.) with proteins such as antibodies which specifically bind the protein marker. The antibodies may be conjugated to any detectable agent (e.g., compound or polypeptide) such as isotopes (e.g., radioisotopes), imaging agents, fluorescent agents, and/or contrast agents. In an alternative method, a secondary binding ligand, such as a second antibody or a biotin/avidin ligand binding arrangement, which can recognize the primary antibody molecules may be conjugated with the agents described above instead of with the primary antibody.

In a particular embodiment, nucleic acid molecules encoding the markers of the instant invention may be detected with nucleic acid molecules (e.g., primers or probes) which specifically hybridize with the nucleic acid encoding the marker (for example by Southern blot, Northern blot, PCR, microarray, etc.).

Antibodies which are immunologically specific for at least one of the markers of the instant invention are also encompassed herein. Compositions comprising at least one antibody of the instant invention and at least one carrier are also encompassed herein. In a particular embodiment, the antibodies may be immobilized on a solid support (e.g., an array or microarray). Indeed, arrays comprising at least one antibody for at least 1, 2, 3, 4, 5, 6, 7, 8, 9, 10, 11, 12, 13, 14, 15, or more of the above markers are also encompassed by the instant invention. In a particular embodiment, the array comprises at least one antibody for each marker of the instant invention. The arrays of the instant invention may also comprise other antibodies such as control antibodies or other neurodegenerative disease (e.g., PD) antibodies. In a particular embodiment, the arrays comprise up to about 20, up to about 25, up to about 50, up to about 100, up to about 500, up to about 1000, up to about 5,000, up to 10,000 or more antibodies (e.g., to unique targets).

Probes and primers which specifically hybridize to at least one of the markers of the instant invention are also encompassed herein. Compositions comprising at least one probe or primer of the instant invention and at least one carrier are also encompassed herein. In a particular embodiment, the probes may be immobilized on a solid support (e.g., an array or microarray). Indeed, arrays comprising at least one probe for at least 1, 2, 3, 4, 5, 6, 7, 8, 9, 10, 11, 12, 13, 14, 15, or more of the above markers are also encompassed by the instant invention. In a particular embodiment, the array comprises at least one probe for each marker of the instant invention. The arrays of the instant invention may also comprise other nucleic acid molecules such as control nucleic acid molecules or other neurodegenerative disease (e.g., PD) markers. In a particular embodiment, the arrays comprise up to about 20, up to about 25, up to about 50, up to about 100, up to about 500, up to about 1000, up to about 5,000, up to 10,000 or more nucleic acid molecules/probes (e.g., to unique nucleic acid targets).

The probes, primers, antibodies, and/or arrays of the instant invention may be incorporated into a kit. The kit may further comprise instruction material, buffers, and/or containers.

In another embodiment of the instant invention, compositions and methods are provided for the detection and/or diagnosis of Parkinson's disease in a subject comprising measuring the function of Treg obtained from the subject, wherein decreased function of Treg is indicative of PD. In a particular embodiment, the decreased function correlates to the severity of PD in the subject. The method may further comprise obtaining or isolating the Treg cells from a biological sample obtained from the subject. In a particular embodiment, the Treg function which is assayed is the ability to suppress responder T cell (Tresp) proliferation.

In addition to the above, the instant invention encompasses methods for screening for therapeutic agents for treating, inhibiting, and/or preventing a neurodegenerative disease (e.g., PD). In a particular embodiment, the method comprises contacting cells with a compound and performing one of the above diagnostic methods (e.g., assessing whether at least one of the above markers is modulated (e.g., closer to wild-type), assessing the amount Tem, measuring Treg function, etc.), thereby identifying a therapeutic agent. In a particular embodiment, the method comprises administering at least one compound to an animal model of a neurodegenerative disease. In a particular embodiment, the method comprises administering the compound to a human with PD. The method may further comprise determining the level of at least one marker of the invention in the subject prior to administration of the compound and determining the level of the marker after administration. The delivered compound may be any natural or synthetic chemical compound (e.g., small molecule compounds (a compound having a molecular weight less than 4,000 atomic mass units (a.m.u.), particularly less than 2,000 a.m.u.), organic or inorganic compounds and molecules, biological macromolecules (such as saccharides, lipids, peptides, proteins, polypeptides and nucleic acid molecules (e.g., those encoding a protein of interest), inhibitory nucleic acid molecule (e.g., antisense, shRNA, miRNA, or siRNA), and drugs (e.g., an FDA approved drug).

Definitions

The singular forms "a," "an," and "the" include plural referents unless the context clearly dictates otherwise.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent, filler, disintegrant, lubricating agent, binder, stabilizer, preservative or vehicle with which an active agent of the present invention may be contained. Acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions.

"Pharmaceutically acceptable" indicates approval by a regulatory agency of the Federal or a state government or listed in the U.S. Pharmacopeia or other generally recognized pharmacopeia for use in animals, and more particularly in humans.

As used herein, a "biological sample" refers to a sample of biological material obtained from a subject, preferably a human subject, including a tissue, a tissue sample, a cell sample, a tumor sample, and a biological fluid (e.g., blood, urine, or amniotic fluid). In a particular embodiment, the biological sample is blood.

As used herein, "diagnose" refers to detecting and identifying a disease or disorder in a subject. The term may also encompass assessing or evaluating the disease or disorder status (severity, progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality). In other words, the term "prognosis" refers to providing a prediction of the probable course and outcome of a disease/disorder or the likelihood of recovery from the disease/disorder.

The term "treat" as used herein refers to any type of treatment that imparts a benefit to a patient afflicted with a disease or disorder, including improvement in the condition of the patient (e.g., in one or more symptoms), delay in the progression of the condition, etc.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10-100, about 10-50, about 15-30, about 15-25, about 20-50, or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 10-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

As used herein, an "instructional material" includes a publication, a recording, a diagram, or any other medium of expression which can be used to communicate the usefulness of the composition of the invention for performing a method of the invention.

The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish.

As used herein, the term "array" refers to an ordered arrangement of hybridizable array elements (e.g., proteins, nucleic acids, antibodies, etc.). The array elements are arranged so that there are at least one or more different array elements on a solid support. In a particular embodiment, the array elements comprise antibodies or oligonucleotide probes.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. Antibody fragments include, without limitation, immunoglobulin fragments including, without limitation: single domain (dAb; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The following examples are provided to illustrate certain embodiments of the invention. They are not intended to limit the invention in any way.

Example 1

Materials and Methods
Subjects and Sample Collection

Blood samples were obtained aseptically by venipuncture from PD patients (n=113) and age- and environment-matched controls (n=96), in two cohorts, a discovery cohort (Cohort A) and a validation cohort (Cohort B). The samples were assessed by flow cytometric analysis of peripheral blood mononuclear cells (PBMC) and used as sources for isolation of CD4+ T cell subsets. Participants were recruited through the University of Alabama at Birmingham (UAB) Movement Disorders Clinic, Neurological Consultants of Nebraska (NCNE), and the Department of Neurological Sciences at the University of Nebraska Medical Center (UNMC). Patients and controls provided written informed consent using IRB-approved forms. PD was diagnosed using UK Brain Bank clinical criteria. Patients and controls with a history of an autoimmune or inflammatory disorder and those receiving chronic immunosuppressive therapy were excluded. Controls were identified from among spouses and caregivers and are hereafter referred to as "caregivers". A brief screening was conducted to exclude caregivers with symptoms likely to represent PD. Data on patients were collected using standard PD-DOC data forms: demographics, primary diagnosis, PD features, diagnostic features, family history, environmental risk, UPDRS-III, and Hoehn and Yahr (HY) stage. At UAB, 50 ml of whole blood were collected in acid citrate dextrose (ACD)-coated tubes (BD Vacutainer®), coded and shipped with an ice pack overnight to the University of Nebraska Medical Center and processed within 24 hours of collection. At NCNE and UNMC, 70 ml of whole blood were collected in heparin-coated tubes (BD Vacutainer®), coded, and stored at room temperature until possessing, which occurred within 2 hours of collection. Complete blood cell count with differential analysis was conducted on blood samples collected in EDTA-coated tubes (BD Vacutainer®; BD, Franklin Lakes, N.J.).

Preparation of Peripheral Blood Mononuclear Cells and T Cells

PBMC were collected by density gradient centrifugation using lymphocyte separation medium per manufacturer's instructions (MP Biomedicals; Santa Ana, Calif.) and either used in proliferation assays, or frozen in fetal calf serum with 10% dimethyl sulfoxide (DMSO) and stored in liquid nitrogen. Additionally, peripheral blood lymphocytes (PBL) were collected by elutriation of healthy donors, and enriched for naïve T cells using CD4+ T Cell Enrichment Columns (R&D Systems) following the manufacturer's instructions with modifications including the addition of antibodies against CD25, CD8, and CD16 (BD Biosciences). Naïve T cells, greater than 94% pure, were frozen in fetal calf serum with 10% DMSO and stored in liquid nitrogen until use as responder T cells (Tresp) in proliferation assays. For proliferation assays, Tresp were thawed and labeled with carboxyfluorescein succinimidyl ester (CFSE) following the manufacturer's instructions (Molecular Probes).

Cell Sorting and Flow Cytometric Analysis of Phenotype and Proliferative Status

Multicolor flow cytometric analysis was performed using a FACSCalibur™ flow cytometer (Becton Dickinson) with fluorochrome-conjugated monoclonal antibodies against the following antigens: CD4 (FITC or Alexa Fluor [AF]-700), CD25 (PE), CD127 (PerCP-Cy 5.5), FoxP3/Scurfin (AF-647), CD95/FAS/Apo1 (APC), CD31/PECAM-1 (AF647), CD39/ENTPD1 (APC), CD49d/Integrin α4 (APC or PE-Cy 7), CD103 (AF-647), CD45RO (APC), CD45RA (AF-700), Integrin β7 (APC), CD29/integrin β1 (AF700) (BD Biosciences, San Jose, Calif.). Isotype-matched mouse or rat monoclonal antibodies were used as negative controls. Data analysis was conducted using BD FACSDiva Software version 6.1.3 (BD Biosciences, San Jose, Calif.). In separate experiments, PBMC that were freshly-isolated from whole blood of PD patients and caregivers, were enriched for CD4+ T cells by negative selection with magnetic beads using Auto-MACS® (Miltenyi Biotec) per manufacturer's instructions. Unstained lymphocytes were used as a negative control, and antimouse Ig, κ/Negative Control Compensation Particles (BD Biosciences) were used to optimize fluorescence compensation settings for fluorescence activated cell sorting (FACS) of CD4+ enriched T cells using a FACSAria™ II (Becton Dickinson). Naïve T cells were identified as CD4+CD25−CD127+, Treg were identified as CD4+CD25+CD127− and Teff were identified as CD4+CD25+CD127+, as expression of the alpha-chain of the IL-7 receptor, CD127, is inversely correlated with expression of FoxP3 and CD4+CD25+CD127−/low Treg are hypo-proliferative and suppressive (Liu et al. (2006) J. Exp. Med., 203:1701-1711; Seddiki et al. (2006) J. Exp. Med., 203: 1693-1700). Cells isolated by FACS were plated with CFSE-labeled Tresp in RPMI 1640 medium supplemented with 10% heat inactivated human AB serum (Atlanta Biologicals Inc.), 2 mM L-glutamine, 55 uM 2-ME, 100 U/ml penicillin, and 100 mg/ml streptomycin, with 25 mM HEPES, 1 mM sodium pyruvate, 1× non-essential amino acids. T cells were activated by engagement of CD3 and CD28 with Dynabeads® (Invitrogen; Grand Island, N.Y.), and proliferation was analyzed on day 3.5 by multicolor flow cytometric analysis.

Gene Expression Analysis

PBMC were thawed and enriched for CD4+ Tcells by negative selection with magnetic beads using AutoMACS® (Miltenyi Biotec; Auburn, Calif.) per manufacturer's instructions. CD4+ Tcells were then cultured for 20 hours in RPMI 1640 medium supplemented with 10% heat inactivated human AB serum, 2 mM L-glutamine, 55 µM 2-ME, 100 U/ml penicillin, and 100 µg/ml streptomycin, with 25 mM HEPES, 1 mM sodium pyruvate, 1× non-essential amino acids with anti-CD3/CD28 Dynabeads (Invitrogen). mRNA was isolated using a RNeasy Mini Kit with on column DNase digestion on a QIAcube according to the manufacturer's protocol (QIAGEN). RNA was stored at −80° C. in RNase-free water. PCR reactions were conducted on Mastercycler® ep gradient S thermal cycler (Eppendorf) using the RT2 Profiler® PCR Array Human Th1-Th2-Th3 (SABiosciences, QIAGEN) and with RT2 SYBR® Green qPCR master mix.

Bioinformatics Correlation Network Creation Via Node Seeding

Cell surface markers that were differentially expressed by flow cytometric analysis in the PD group compared to caregivers were used to build networks for correlation analysis. Nodes in the networks represent cell surface markers. Edges represent the weighted correlation of each gene and an associated p-value. Correlations with p-value >0.0005 were not considered statistically significant and edges outside that threshold were discarded; all correlations met this threshold. Edge width and opacity refers to strength of correlation (positive or negative correlation).

Statistical Analysis

Fisher's exact tests were used to examine the association of categorical participant characteristics with disease status. A two-sample t-test was used to examine the association of age with disease status. Normality of flow cytometric data was assessed using the Anderson-Darling test. Since many of the flow cytometric measures did not pass the test for normality, values were compared between caregivers and PD patients using a non-parametric Mann-Whitney test. To control for the false discovery rate at the α level, p values obtained from comparing flow cytometric data of caregivers and PD patients were adjusted using Benjamini-Hochberg adjustment for multiple comparisons. Pearson product-moment correlation coefficients were used to determine correlations between antigens measured by flow cytometric analysis and UPDRS-III score, and FAS and CD45RO. Linear regression was used to determine if age or UPDRS-III score predict variables measured by flow cytometry.

Associations of flow cytometric data (CD45RO+RA−, FAS and α4β7) with UPDRS-III scores (binned into 3 groups), were assessed using Kruskal-Wallis non-parametric ANOVA with post hoc pairwise comparisons of PD patients verses controls conducted with Dunn's multiple comparison test. Regression analysis was used to adjust for gender; a general linear model on rank-transformed CD31 values was used to evaluate CD31 and UPDRS-III followed by a Bonferroni adjustment for multiple comparisons. Statistical analyses were conducted using Prism (GraphPad Software, Inc) or IBM SPSS (IBM).

Results

Data from two cohorts of PD patients and caregivers was collected; a discovery cohort (Cohort A) and a validation cohort (Cohort B). Descriptive statistics of Cohorts A and B demonstrate that gender, and self-reported exposure to pesticides (Cohorts A and B), chemical solvents and heavy metals (Cohort B) were associated with PD (FIG. 8). More importantly, both cohorts were comprised of PD patients and caregivers that were similar between cohorts with respect to age, disease duration, motor function and disease severity; the latter two scored by practicing neurologists using part III of the United Parkinson's Disease Rating Scale (UPDRS), the most commonly used assessment of disease severity (Leddy et al. (2011) Phys. Ther., 91:102-113). In the pilot study, Cohort A, whole blood samples from PD patients (n=41) and caregivers (n=31) were evaluated by flow cytometric analysis in an un-blinded fashion to investigate phenotypic leukocyte antigens of interest. Those analyses indicated that peripheral immune T cell phenotypic changes resided in the CD4+ T cell, CD4+CD25+CD127− Treg and CD4+CD25+CD127+ Teff populations in PD, and that the percentage of effector/memory T cells (Tem) were increased (FIG. 9). Based on these preliminary results, a prospective blinded study was designed for a second, but larger, validation cohort, Cohort B, consisting of 72 PD patients and 65 caregivers (FIG. 8).

Lymphocyte and CD4+ T Cell Frequencies in PD

Figure 2:
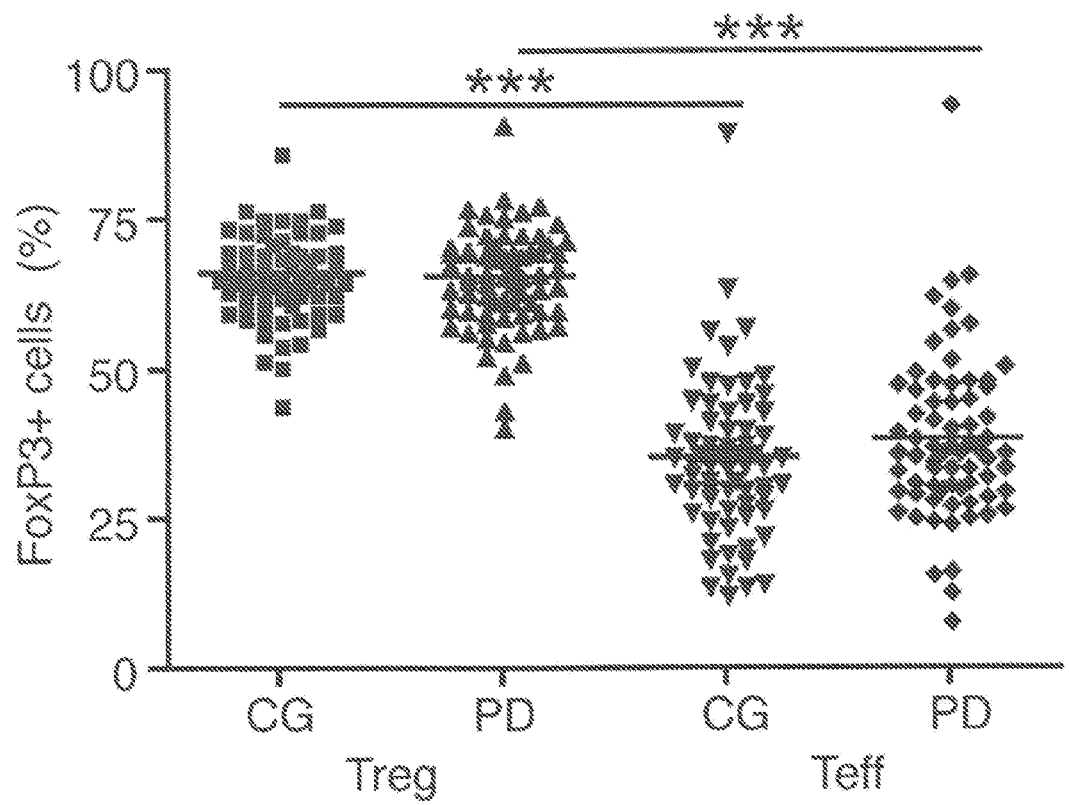
FIG. 2 shows the percentages of FoxP3+ Treg and Teff from PD patients and caregivers. Data are the percentages of FoxP3 positive Treg and Teff with medians (horizontal lines). Significant differences among groups were determined by Kruskal-Wallis nonparametric ANOVA, and pair-wise comparisons determined by Dunn's multiple comparison's post-hoc analysis where $***p \leq 0.001$.

To define changes in the numbers and phenotype of CD4+ T cells, Treg and Teff of PD patients in Cohort B, flow cytometric analyses of peripheral blood mononuclear cells (PBMC) from PD patients and caregivers were conducted. CD4+ T cell populations were identified by high expression of CD4 and low side scatter, and Treg and Teff were identified within the CD4+ T cell population as CD25+ CD127− and CD25+CD127+, respectively (Liu et al. (2006) J. Exp. Med., 203:1701-1711; Seddiki et al. (2006) J. Exp. Med., 203:1693-1700) (FIG. 1A). To confirm identification of Treg, the intracellular transcription factor forkhead box P3 (FoxP3) was measured. As expected, the percentage of FoxP3+ Treg was consistently and significantly higher than the percentage of FoxP3+ Teff in both PD patients and caregivers, indicating that CD4+CD25+CD127− Tcells are Treg (Liu et al. (2006) J. Exp. Med., 203:1701-1711) (FIG. 2). CD4+ T cell frequency was decreased in PD patients compared to caregivers (FIG. 1B), while no significant differences were seen in the percentages of Treg and Teff amongst PD patients and caregivers (FIG. 2).

To determine whether the decreased percentage of CD4+ T cells in cohort B was due to reductions in the absolute number of CD4+ T cells or an increase in other lymphocyte populations, complete blood count (CBC) and differential counts of PD patients were compared to caregivers. Hemoglobin concentrations, total white blood cell, absolute lymphocyte and CD4+ T cell counts were assessed for Cohort B (FIG. 10). Compared to caregivers, PD patients presented diminished percentages of lymphocytes and decreased absolute lymphocyte counts with increased percentages of neutrophils. Using the CD4+ T cell percentages from flow cytometric analyses and absolute lymphocyte counts from differentials, absolute CD4+ T cell counts were calculated, which were significantly decreased in PD patients compared to caregivers.

Increased Effector/Memory CD4+ T Cells in PD

Phenotypic changes in the CD4+ T cell, Treg and Teff populations were assessed by flow cytometric analysis (FIG. 9). CD4+ T cells from PD patients demonstrated increased percentages of CD45RO+ events and FAS+ events than caregivers, while the percentages of CD45RA+ and CD31+ CD4+ T cell events were decreased in PD. The percentages of integrin α4β7+ cells were decreased significantly in PD patients, and integrin α4β1+ CD4+ T cells were elevated slightly, though not significantly (p=0.08). Within the Teff and Treg populations, FAS+ Teff were increased and CD45RA+ Teff were significantly decreased in PD patients compared to caregivers, while there were no differences observed in the Treg population. Significant differences in phenotypic markers of CD4+ T cell subsets determined by Mann-Whitney comparison remained significant after Benjamini-Hochberg adjustment for multiple comparisons (FIG. 11). Although gender was associated with disease status (FIG. 8), the percentages of CD45RO+, FAS+ and integrin α4β7+ events amongst the CD4+ T cell population of the PD group remained significantly different from that of the caregiver group after adjusting for gender. However, the percentages of CD4+ T cells and the percentages of CD4+ T cells expressing CD45RA, CD31, and integrin α4β1 were not significantly different after adjusting for gender.

Figure 3:
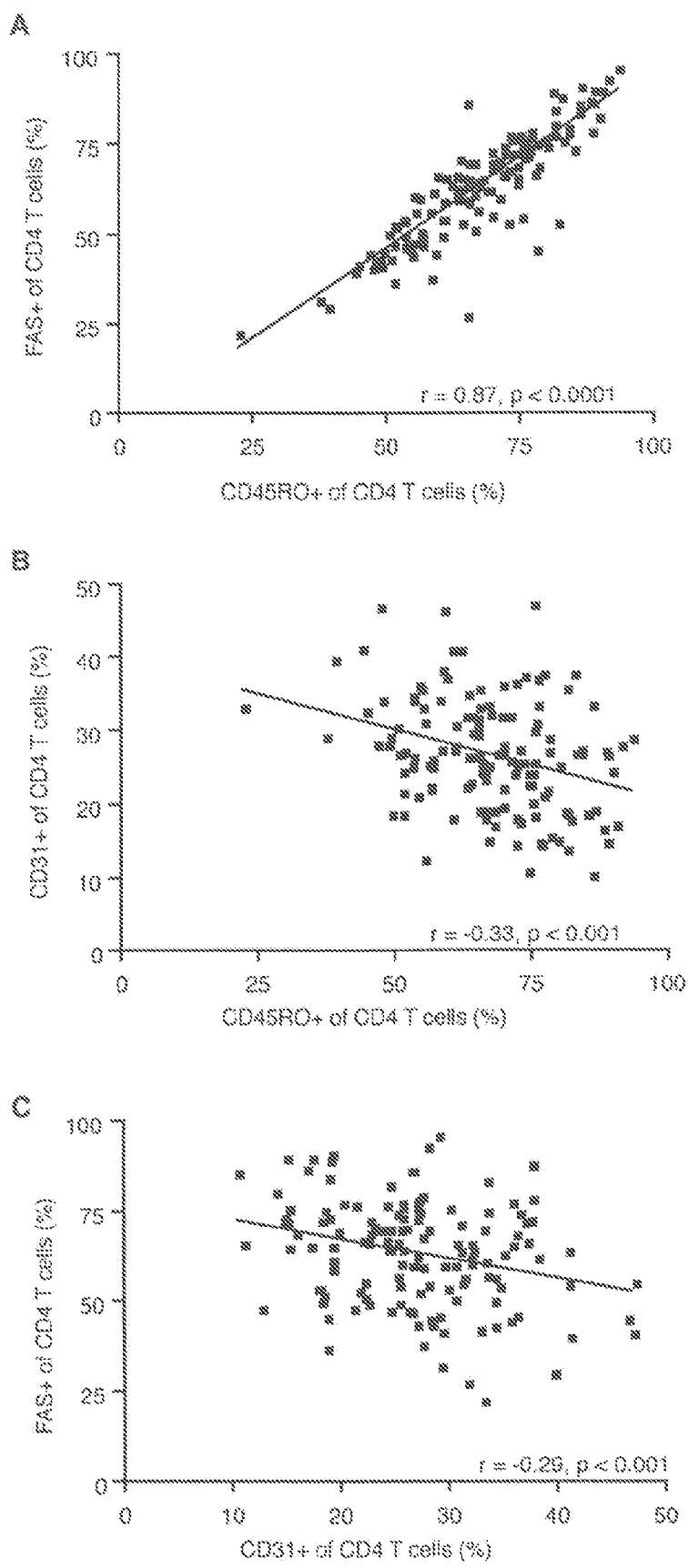
FIG. 3 shows that the percentages of CD45RO+, FAS+ and CD31+CD4+ T cells are correlative.

CD45RO+CD4+ T cells increase with age (Douek et al. (1998) Nature 396:690-695). However, the mean age of PD patients compared to caregivers were not significantly different (FIG. 8), indicating that the increase in the percentages of CD45RO+CD4+ T cells in PD patients compared to caregivers was not age-associated. Previous studies have demonstrated that a high percentage of CD45RO+ memory CD4+ T cells are FAS+ (Miyawaki et al. (1992) J. Immunol., 149:3753-3758), and as expected, regardless of diagnosis, the percentages of CD45RO+CD4+ T cells and FAS+CD4+ T cells were found to be strongly correlated (FIG. 3A). In addition, a moderate negative correlation between percentages of CD45RO+CD4+ T cells and CD31+ CD4+ T cells was found among all Cohort B participants (FIG. 3B), and a weak negative correlation between the percentages of CD31+ and FAS+CD4+ T cells was found (FIG. 3C).

Association of Disease Severity with T Cell Phenotypes

Figure 4:
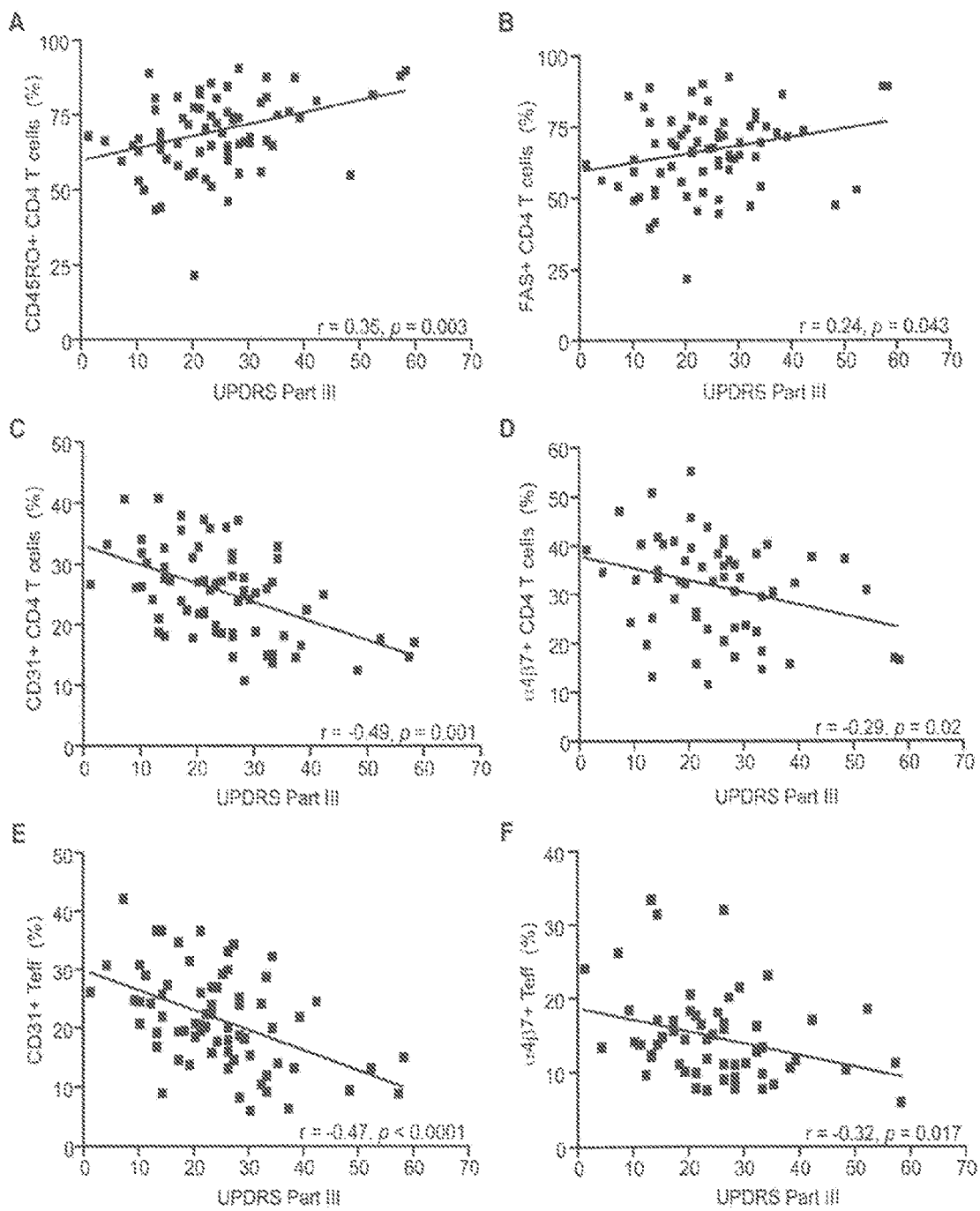
FIG. 4 shows that CD4+ T cell and Teff phenotypes are associated with UPDRS-III score and as such a marker for advancing disease rather than disease duration or age.

The relationship of phenotypic alterations in CD4+ T cells, Treg and Teff was assessed with age, clinical measures of disease severity and disease duration. Linear regression demonstrated that age was not predictive of the variation in the percentage of CD4+ T cells that were CD45RO+ in PD patients ($r^2=0.044$, p00.13) or caregivers ($r^2=0.003$, p>0.05). A moderate positive correlation was found between UPDRS-III score and the percentages of CD45RO+CD4+ T cells (FIG. 4A), and a weak positive correlation between UPDRSIII score and the percentage of FAS+CD4+ T cells was also found (FIG. 4B). The percentages of CD31+ CD4+ T cells demonstrated a strong negative correlation with UPDRS-III (FIG. 4C) and integrin α4β7+ CD4+ T cells showed a moderate negative correlation with UPDRS-III (FIG. 4D). CD45RO expression by Teff was weakly correlated with UPDRS-III (Pearson r=0.24), while CD31 expression on Teff showed a strong negative correlation with UPDRS-III score (FIG. 4E), and α4β7+ Teff showed a moderate inverse correlation with UPDRS-III score (FIG.

4F). No correlations of disease duration as measured by years since diagnosis could be established for percentages of CD45RO+, FAS+, CD31+, or integrin α4β7+ CD4+ T cells.

Figure 5:
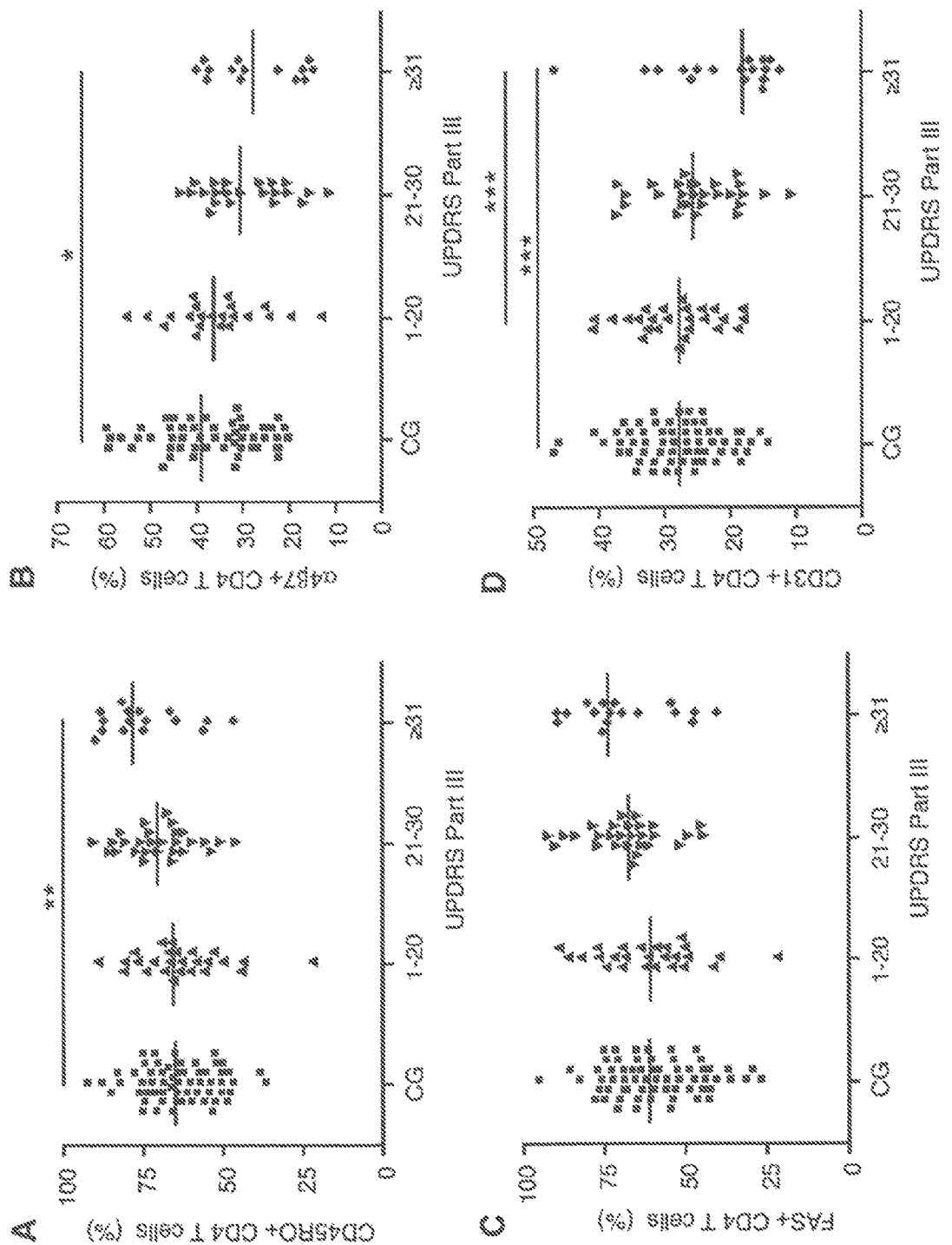
FIG. 5 shows that CD4+ T cell and Teff phenotypes are associated with UPDRS-III score. Flow cytometric data of caregivers and PD patients from Cohort B were binned into 4 groups based on UPDRS-III scores: caregivers (CG, n=61), 1-20 (n=25), 21-30 (n=28), and ≥31 (n=16). The percentages of CD4+ T cells expressing CD45RO (FIG. 5A), α4β7 (FIG. 5B), FAS (FIG. 5C), and CD31 (FIG. 5D) in each group were associated with UPDRS-III group (p<0.05). Percentages of CD45RO+ (FIG. 5E) and CD31+ (FIG. 5F) Teff and the percentages of α4β7+(FIG. 5G) and CD31+ (FIG. 5H) Treg in each group were associated with UPDRS-III group (p<0.05). Data are the percent-positive of T cells with medians (horizontal lines). Significant differences among groups were determined by Kruskal-Wallis nonparametric ANOVA (CD45RO, α4β7 and FAS) or by general linear model (CD31), and pair-wise comparisons were determined by either Dunn's or Bonferroni adjustments for multiple comparisons (CD31) where $*p \leq 0.05$, $p \leq 0.01$, and $*p \leq 0.001$.
Figure 5:
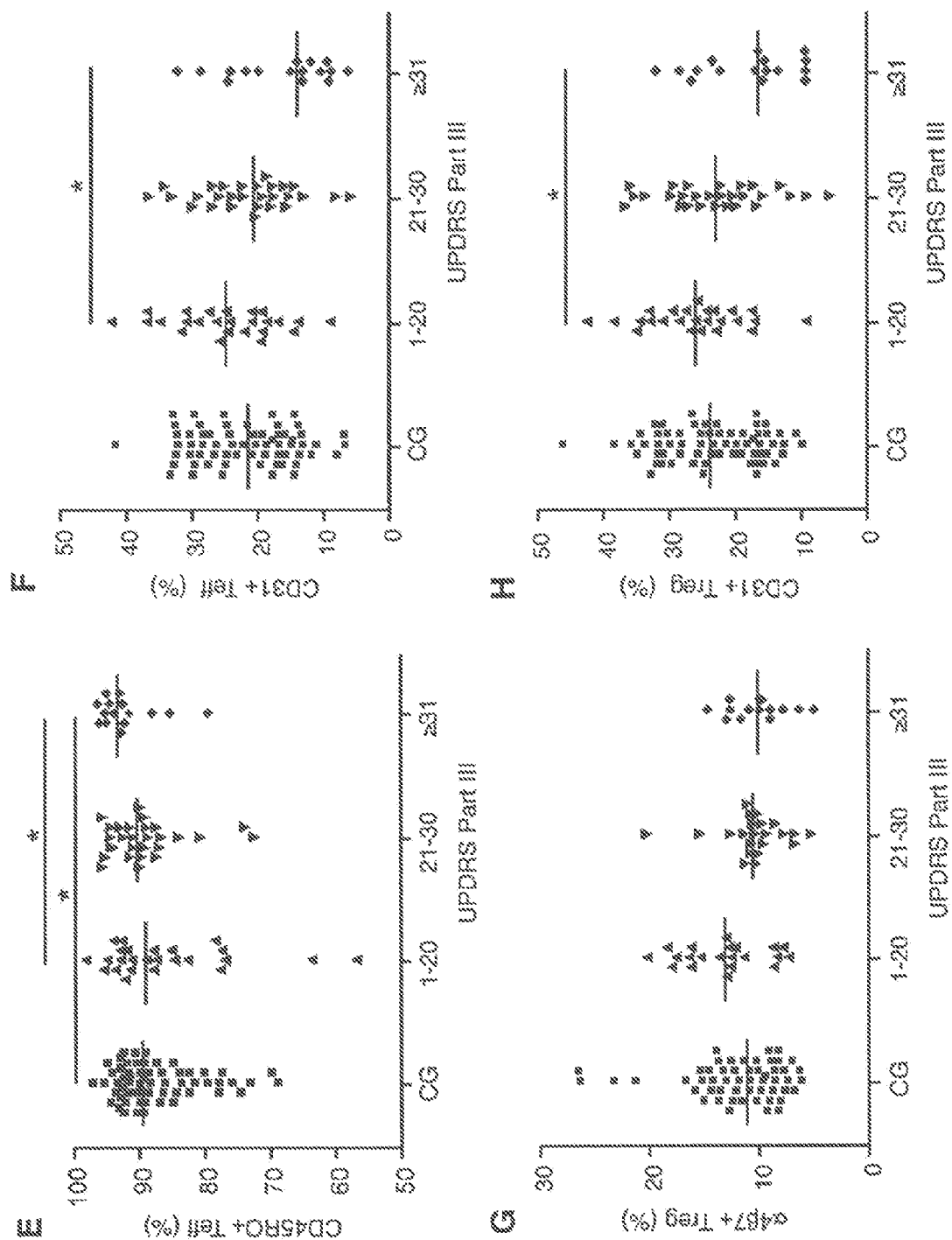

To further investigate the relationship between disease severity and CD4+ T cells, flow cytometric data was assessed of caregivers and PD patients segregated into 3 groups based on UPDRS-III scores of: 1-20 (n=25), 21-30 (n=28), and ≥31 (n=16). Nonparametric ANOVA indicated differences among groups with respect to the percentages of CD45RO+, α4β7+, and FAS+ CD4+ T cells (FIG. 5A-5C), and Dunn's adjustment for multiple comparisons demonstrated that the significant differences occurred between caregivers and PD patients with a UPDRS-III score ≥31 with respect to the percentages of CD45RO+ and α4β7+ CD4+ T cells. After adjusting for gender, there was a significant association between CD31 and UPDRS-III score, and Bonferroni adjustment for multiple comparisons revealed a significant difference between controls and PD patients with UPDRS-III score ≥31 and PD patients with a UPDRS-III score of 1-20, compared to those with a UPDRSIII score ≥31 (FIG. 5D). In the Teff population, CD45RO+ was associated with UPDRS-III, with significant differences occurring between PD patients with a UPDRS-III score ≥31 and caregivers and those with a score between 1 and 20 (FIG. 5E). After adjusting for gender, percentages of CD31+ CD4+ T cells were associated with UPDRS-III, and Bonferroni adjustment for multiple comparisons demonstrated that PD patients with UPDRS-III scores of 1-20 were significantly different from those with a score ≥31 (FIG. 5F). In the Treg population, the percentages of CD45RO+ and FAS+ cells were not associated with UPDRS-III scores, but α4β7+ Treg percentages were associated with UPDRS-III (FIG. 5G). After adjusting for gender, percentages of CD31+ Treg were associated with UPDRSIII scores, wherein Bonferroni adjustment for multiple comparisons demonstrated that the percentages of CD31+ Treg in PD patients with a UPDRS-III score ≥31 were significantly less than those from patients with scores of 1-20 (FIG. 5H).

Figure 6A:
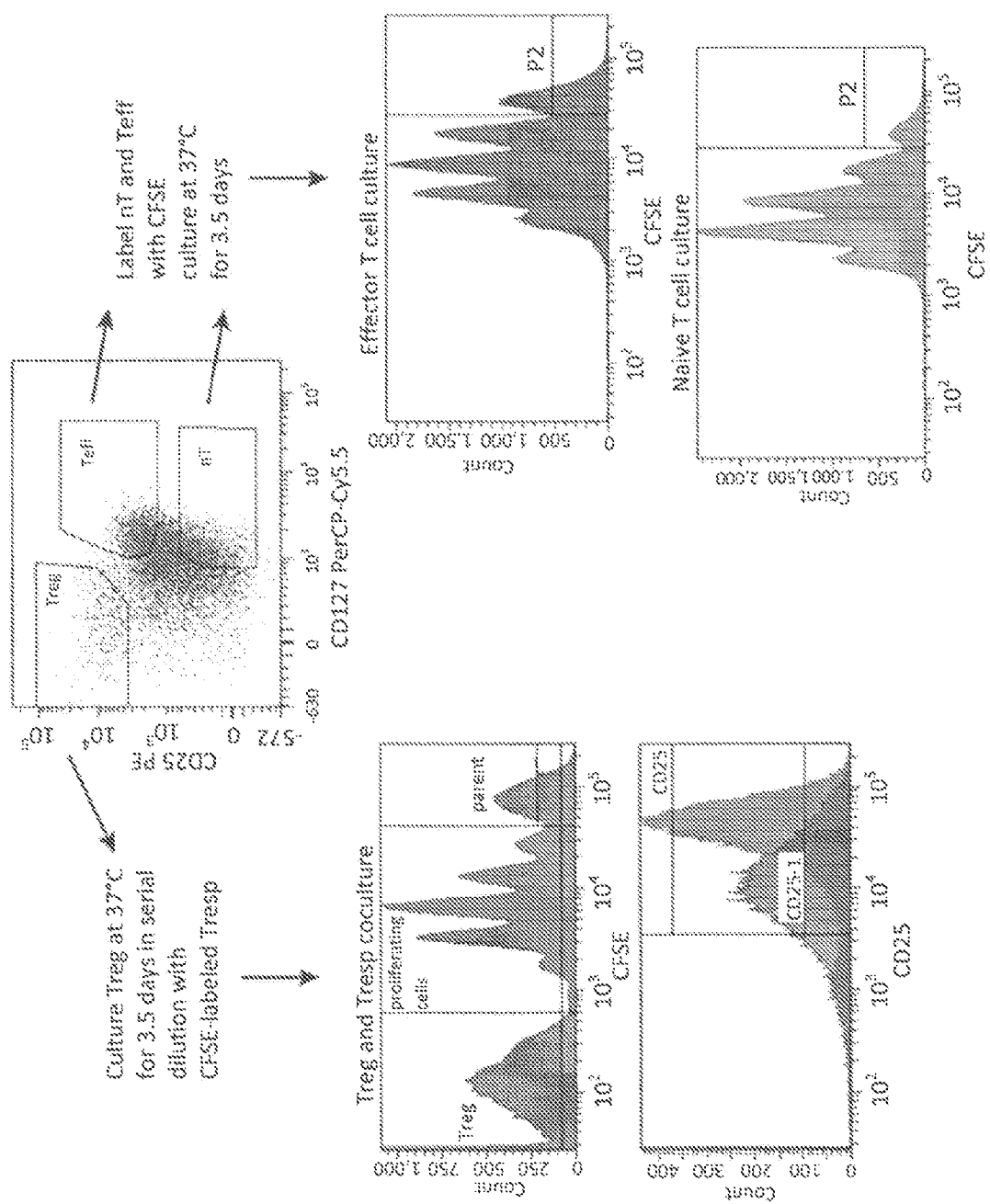
FIG. 6A shows that Treg, nT and Teff were identified within the CD4+ T cell population as CD25hiCD127−, CD25−CD127+, and CD25+CD127+, respectively (top, center dot plot). CFSE-labeled CD4+ CD25− allogeneic responder T cells (Tresp) were co-cultured with serially-diluted Treg. By flow cytometric analysis, CFSE was measured to determine the percentage of Tresp that proliferated, and the percentage of CD25+ Tresp was measured as an indication of activation (histograms, left panels). The proliferative capacities of isolated CFSE-labeled Teff and nT was measured by flow cytometric analysis of CFSE (histograms, right panels).
Figure 6:
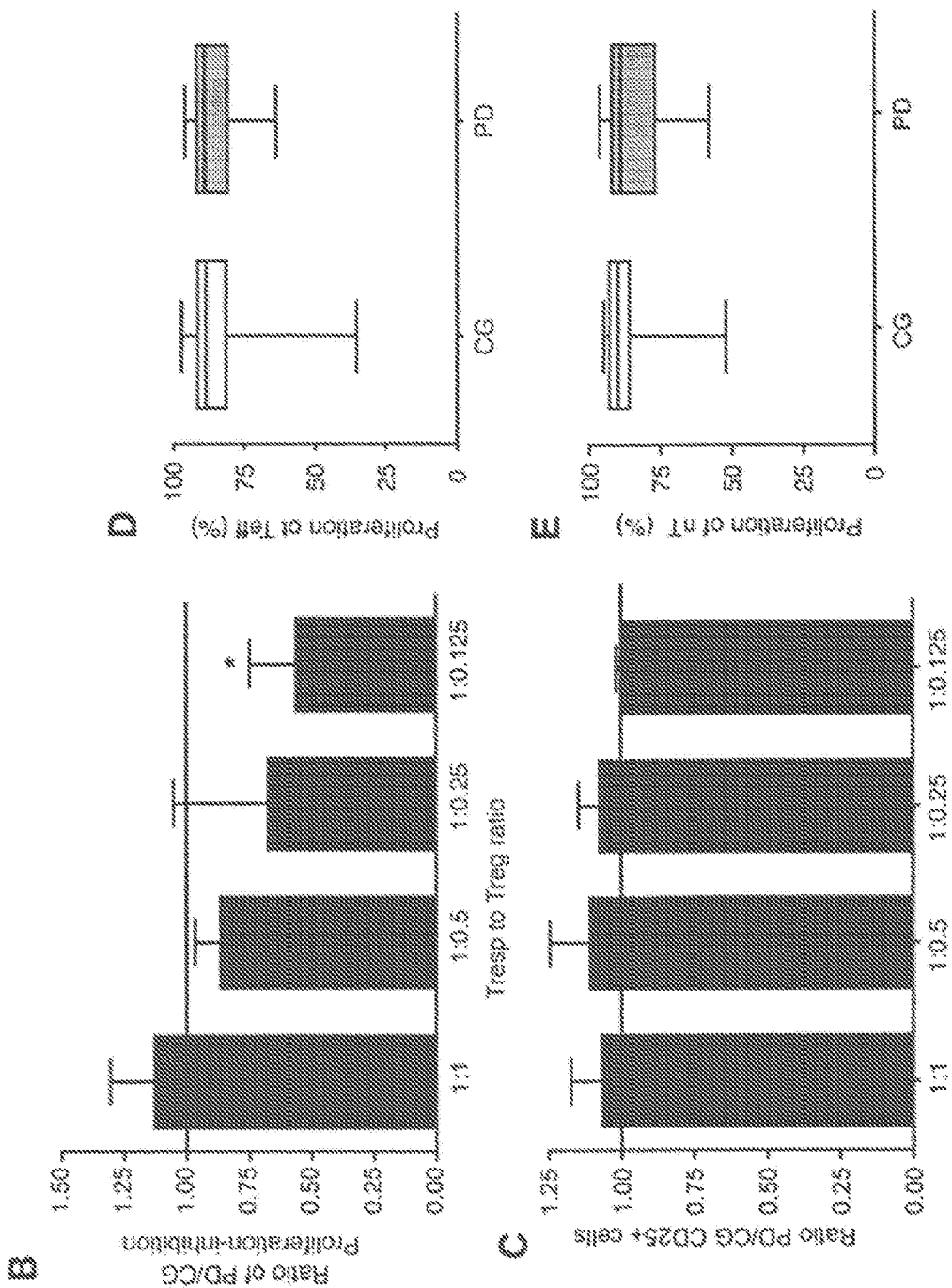
FIG. 6 shows that Treg from PD patients are dysfunctional while CD4+ naïve T cells (nT) and Teff show no alterations in proliferative capacity.

Treg Suppressive Function, but not CD4+ T Cell Proliferative Capacity is Affected in PD In vitro functional assays were then conducted to determine whether Treg isolated from PD patients had reduced ability to suppress the proliferation of CD4+CD25− responder T cells (Tresp) from healthy allogeneic donors. CD4+CD25hiCD127− Treg, CD4+CD25−CD127hi naïve T cells and CD4+CD25+CD127hi Teff were isolated by fluorescence-activated cell sorting from PBMC of PD patients and caregivers (FIG. 6A). Treg were serially-diluted and co-cultured with anti-CD3/anti-CD28-coated beads and a constant number of CSFE-labeled Tresp. As indicators of T cell activation and proliferation, CD25 was measured for the former and the loss of CSFE was measured for the latter by flow cytometric analysis (FIG. 6A, left histograms). It was first tested whether Treg from PD patients compared to caregivers would equally suppress proliferation of Tresp at all dilutions (PD/CG, Treg-mediated suppression=1). It was found that PD Treg showed decreased ability to suppress Tresp proliferation at the greatest dilution (1:0.125) (FIG. 6B). This may indicate that microenvironments in which Treg are greatly outnumbered, differentially inhibit Treg function in PD compared to caregivers. CD25 expression on T cells increases upon activation (Depper et al. (1984) J. Immunol., 133:3054-3061), and thus should be inhibited in the presence of Treg. Indeed, CD25 expression was correlated with Treg dilution for PD patients ($r^2$=0.48, p<0.001) and caregivers ($r^2$=0.67, p<0.001). However, Treg from PD patients did not suppress expression of CD25 differentially than caregivers (FIG. 6C, PD/CG, Treg-mediated suppression=1). To determine if the increase in memory T cell phenotype in PD is due to hyperproliferative naïve T cells (nT) or effector T cells (Teff), the proliferative response of Teff and nT after CD3/CD28 stimulation were measured (FIG. 6A, right histograms). No significant differences in proliferative capacity of Teff (FIG. 6D) or nT (FIG. 6E) were found between PD patients and caregivers suggesting that aberrant proliferation of nT or Teff does not contribute to the phenotypic skewing towards Tem.

CD27 mRNA is Decreased, while IL-9 and IL-6 are Increased in CD4+ T Cells from PD Patients To elucidate potential causes of phenotypic changes in the CD4+ T cell population, quantitative reverse transcription polymerase chain reaction (qRT-PCR) was conducted for gene expression associated with helper T cell phenotypes in CD3/CD28-activated CD4+ T cells from PD patients (n=7) and caregivers (n=9). mRNA levels of the anti-apoptotic cytokine, IL-9, were increased by 3.1-fold. IL-6 mRNA levels were significantly increased by 2.3-fold, while CD27 mRNA expression was diminished by 1.6-fold. Memory T cells have been shown to increase IL-9 production after anti-CD3/CD28 stimulation in vitro (Soler et al. (2006) J. Immunol., 177:6940-6951). IL-6 is associated with chronic inflammatory responses (Gabay, C. (2006) Arthrit Res. Ther., 8:S3), and CD27 expression is reduced on mature lymphocytes (Hintzen et al. (1993) J. Immunol., 151:2426-2435). Thus, these data further support the results demonstrating chronic inflammatory responses in PD and skewing of CD4+ Tcells towards the Tem phenotype.

Bioinformatics Networks Propose a PD Immunophenotype

Figure 7:
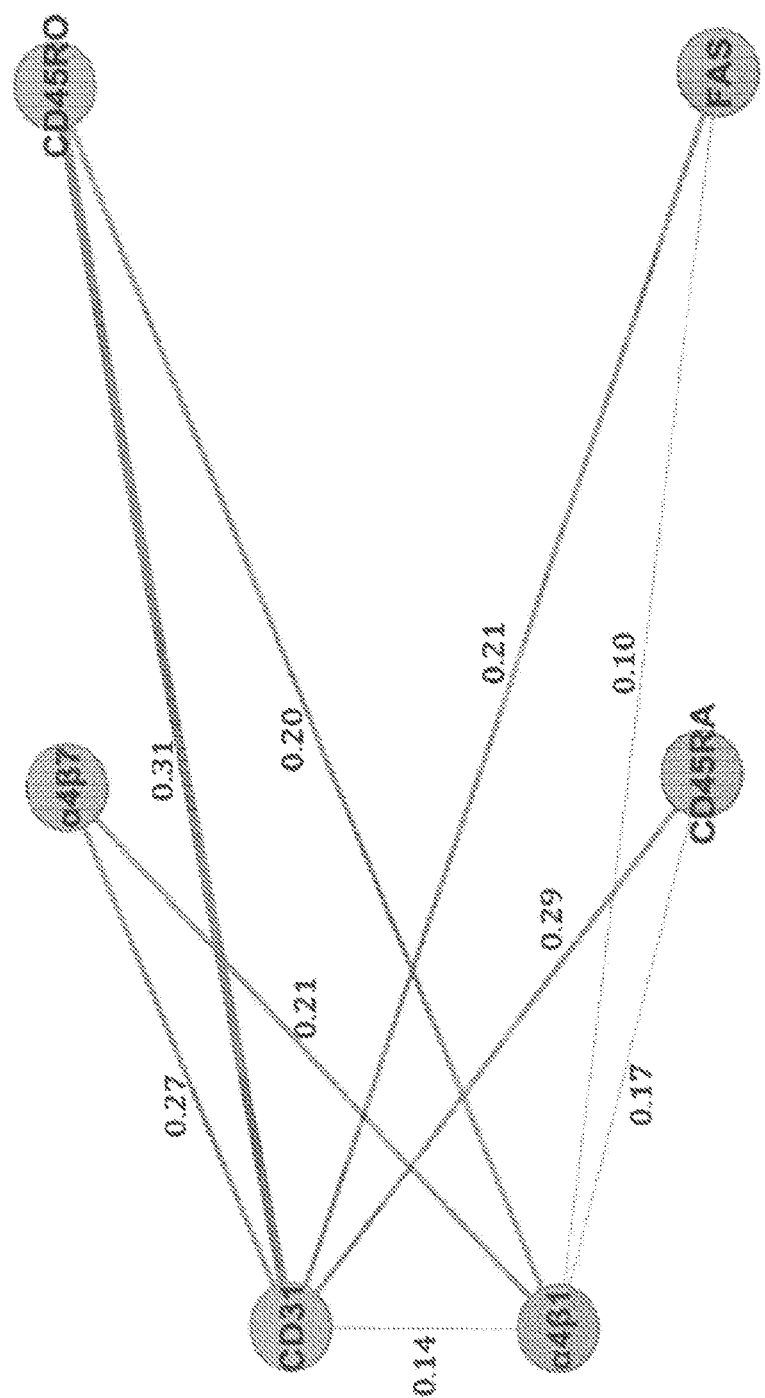
FIG. 7 shows the correlation difference networks of caregivers and PD patients. Differences network interactions are demonstrated by the correlation difference network, where edge width and opacity reflect the correlation difference score (n=37 CG, 46 PD). Correlations with p-value >0.0005 were not considered statistically significant, and edges outside that threshold were discarded.

Flow cytometric analyses (FIG. 11, FIG. 4, and FIG. 5) indicate that phenotypic markers of Tem are linked to PD. To investigate associations among phenotypic markers of Tem, bioinformatics were used to conduct pair wise computations of Pearson correlations for each possible combination of phenotypic markers within each dataset (PD patient and caregiver). The absolute differences in the correlation scores of the edges of the PD and caregiver networks were calculated and are presented as a Correlation Difference Network (FIG. 7). The network structures for both the PD and caregiver groups were conserved fairly strongly. While the edges emanating from CD31 consisted of the strongest differences in correlation, the association of CD31 with gender most likely contributes to this difference. The weaker correlation coefficient of α4β7 with α4β7 in PD compared to that of caregivers indicates that the increased variation in the CD4 T cell pool of PD patients is due to the increased percentage of integrin α4β7+ CD4+ T cells. Similarly, the difference in the correlation coefficients of α4β1 with CD45RO in PD patients compared to caregivers is likely due to the increased percentage of CD45RO+ CD4+ T cells in PD. Thus, these data further support the accumulation of Tem in PD patients.

This report demonstrates associations between PD, environmental exposures, gender, effector memory T cells (Tem) and Treg function. The present studies demonstrate that changes in CD4+ T cell, Treg and Teff phenotypes are associated with motor function scores determined by UPDRS-III; the most commonly used assessment of disease severity (Leddy et al. (2011) Phys. Ther., 91:102-113). Moreover, PD patients with UPDRS-III scores of 30 or higher had increased CD45RO+ and FAS+ CD4+ T cells and decreased α4β7+ and CD31+ CD4+ T cells; indicative of increased effector/memory T cells. Despite best medical management provided to PD patients, UPDRS scores increase over time and parallel disease progression (Holloway, R. (2009) Arch. Neurol., 66:563-570). Thus, the UPDRS-III "on medication" score is a reasonable proxy for disease severity. This report has associated PD motor severity with T cell phenotypes. Specifically, the predominance of Tem in more severe stages of disease supports a role of chronic immune activation in disease progression.

PD is a disease of the nervous system and engagement of peripheral T cell responses seems ill-connected. However, mounting evidence implicates both the innate and adaptive immune systems in the pathobiology of PD. Aberrant species of α-Syn in Lewy bodies are linked to microglial activation, oxidative stress, neuroinflammation, and loss of dopaminergic neurons in affected brain regions (Czlonkowska et al. (1996) Neurodegeneration 5:137-143; Zhang et al. (2005) FASEB J., 19:533-542; Reynolds et al. (2008) J. Neuroimmune Pharmacol., 3:59-74). The same protein species are also found in the periphery (Beach et al. (2010) Acta Neuropathol., 119:689-702). Nitrated-α-Syn, but not unmodified α-Syn is found in cervical lymph nodes of MPTP-treated mice (Benner et al. (2008) PLoS One 3:e1376), and modified forms of α-Syn are in gut tissue of PD patients (Lebouvier et al. (2010) PLoS One 5:e12728; Forsyth et al. (2011) PLoS One 6:e28032). The presence of modified forms of α-Syn in lymph nodes and gut tissues present a means for neoantigen exposures and activation of the adaptive immune system. To test this hypothesis, it was investigated whether N-α-Syn-specific T cells adoptively transferred to MPTP-intoxicated recipient mice could play a role in nigrostriatal degeneration. It was observed that vasoactive intestinal peptide (VIP)-induced natural regulatory T cells (Treg) were neuroprotective, while N-α-Syn-specific helper T cells (Th1 and Th17) exacerbated MPTP-induced neuronal degeneration (Reynolds et al. (2010) J. Immunol., 184:2261-2271). Therefore, it was further hypothesized that alterations in the frequency, phenotypes or function of CD4+ T cells, Treg and Teff are operative in PD patients and associated with disease severity or duration. This study demonstrates that T cell phenotypes, specifically those of the effector/memory lineage, are associated with clinical outcomes of disease severity.

The relative lymphopenia in PD could be caused by FAS-mediated apoptosis related to CD25 (Bas et al. (2001) J. Neuroimmunol., 113:146-152). Indeed, increased lymphocyte FAS expression in PD patients was observed (Calopa et al. (2010) Neurobiol. Dis., 38:1-7). However, increases in apoptosis may not be due to FAS alone (Calopa et al. (2010) Neurobiol. Dis., 38:1-7). In addition to an increase in FAS, diminished CD31 expression was observed, which was associated with disease severity. CD31, or platelet endothelial cell adhesion molecule-1 (PECAM-1), is expressed on most naïve CD4+ T cells, but is decreased on naïve T cells undergoing homeostatic proliferation (Azevedo et al. 2009) and on effector memory T cells (Ashman et al. (1991) Tissue Antigens 38:208-212; Demeure et al. (1996) Immunology 88:110-115), particularly those activated by the T cell receptor (Kohler et al. (2009) Blood 113:769-774). Using qRT-PCR, no detectable diminution of CD31 mRNA transcripts in PD patients was found; a finding that is not unexpected since CD31 is not regulated at the transcript level (Formasa et al. (2010) J. Immunol., 184:5485-5492). Under normal conditions, CD31-signaling controls the amplitude of clonal expansion and is required for establishment of regulatory functions and T cell tolerance (Lebouvier et al. (2010) PLoS One 5:e12728) by negatively regulating TCR-mediated signal transduction (Newton-Nash et al. (1999) J. Immunol., 163: 682-688; Kohler et al. (2009) Blood 113:769-774). Recent studies using CD31 deficient mice support the role of CD31 in controlled T cell activation and survival, and demonstrate that loss of CD31 increases T cell susceptibility to apoptosis (Ross et al. 2011). Thus, the decrease in CD31 on PD CD4+ T cells, particularly in those with advanced motor dysfunction, may contribute to the decrease in CD4+ T cell counts by increasing apoptosis. In addition, while $CD31^{-/-}$ mice are known to display normal numbers of CD25+FoxP3+ Treg, $CD31^{-/-}$ Treg have impaired regulatory function at low Treg:Tresp ratios (Lebouvier et al. (2010) PLoS One 5:e12728). Here, it was found that the percentages of CD31+ Treg in PD patients negatively correlated with disease severity, and Treg function was reduced at low Treg:Tresp ratios. The negative correlation and association of CD31 with disease severity and the memory phenotype indicate that decreased CD31 may be attributed to increased T cell activation (Kohler et al. (2009) Blood 113:769-774), yet it is possible that the loss of CD31 is also aberrant and contributes to decreased Treg function in PD as seen in $CD31^{-/-}$ mice.

CD45RO+CD4+ T cells increase in PD (Fiszer et al. (1994) Acta Neurol. Scand., 90:160-166; Bas et al. (2001) J. Neuroimmunol., 113:146-152; Calopa et al. (2010) Neurobiol. Dis., 38:1-7). Additional markers of memory T cells are also differentially expressed in PD. The observed increase in CD45RO+ and decrease in CD45RA+CD4+ T cells paralleled the increase in FAS+CD4+ T cells and decrease in CD31+ CD4+ T cells, which are characteristics of activated or proliferating T cells (Oyaizu et al. (1994) Blood 84:2622-2631; Demeure et al. (1996) Immunology 88:110-115). In this context, the instant results demonstrating decreased expression of CD27 at the mRNA level in the CD4+ T cell population indicates that the Tem phenotype is increased in PD (Hintzen et al. (1993) J. Immunol., 151:2426-2435). Tem and central memory T cells (Tcm) are distinct subsets of memory T cells defined by function (Pepper et al. (2011) Nat. Immunol., 12:467-471). The Tem pool contains Th1, Th2, and cytotoxic T cells that migrate to inflamed peripheral tissues and have immediate effector function, while Tcm home to secondary lymphoid tissues and have little effector function, but are able to proliferate and differentiate into effector T cells (Th1, Th2, Th17) in response to antigenic stimulation (Sallusto et al. (2004) Annu. Rev. Immunol., 22:745-763). Both memory T cell subsets are highly responsive to antigenic stimulation, but have reduced proliferative capacity and an increased propensity to undergo apoptosis (Sallusto et al. (1999) Nature 401:708-712; Sallusto et al. (2004) Annu. Rev. Immunol., 22:745-763). This lends further support to the observed relative lymphopenia and reduced CD4+ T cell numbers in PD found here. The co-stimulatory molecule, CD27 functions to promote survival of activated and memory T cells and to generate the effector T cell pool (Hendriks et al. (2003) J. Exp. Med., 198:1369-1380). However, memory T cells acquire the CD45RA−CD27− Tem phenotype after chronic antigenic stimulation (De Jong et al. (1992) Eur. J. Immunol., 22:993-999). These data support a predominating Tem cell phenotype in PD patients, which is a significant finding as it strongly indicates that PD has chronic inflammatory components at play in the periphery. This is further supported by the observation that chronic infection, and thus chronic antigenic stimulation, leads to decreased expression of CD31 and CD27 (Yonkers et al. (2011) J. Infect. Dis., 203:635-645).

A significant decrease in α4β7+ CD4+ T cells was also observed along with a slight increase in α4β1+ CD4+ T cells in PD patients compared to caregivers. Low expression of α4β7 and high expression of α4β1 are characteristic of brain-tropic T cells (Denucci et al. (2009) Crit. Rev. Immunol., 29:87-109), as the interaction between α4β7 and mucosal addressin cell adhesion molecule 1 (MAd-CAM-1) allows for entry into the gut (Agace, W. W. (2006) Nat. Rev. Immunol., 6:682-692), and α4β1 and vascular cell adhesion molecule 1 (VCAM-1) on endothelial cells allows for entry of T cells into the brain (Engelhardt et al. (2005) Trends Immunol., 26:485-495). While the observed increase in α4β1+CD4 T cells in the current study was not overtly significant and was associated with gender, the significant decrease in α4β7+ CD4 T cells alone is indicative of brain tropic T cells. These data may also indicate an increase in inflammatory responses in the gut. Increased expression of MAdCAM-1 on endothelial cells in inflamed gut tissue augments α4β7+ T cell homing and compartmentalization to the gut, leading to decreased frequency of in α4β7+ T cells in the peripheral blood (Di Sabatino et al. (2009) Hum. Pathol., 40:699-704). No studies have yet to investigate inflammation per se in gut tissue of PD patients. However, studies of PD gut tissue have demonstrated the presence of proinflammatory immune mediators (Lebouvier et al. (2010) PLoS One 5:e12728; Forsyth et al. (2011) PLoS One 6:e28032). Histopathological studies of PD gut mucosa demonstrate increased intestinal permeability, which correlated with *E. coli* bacteria, nitrotyrosine and α-Syn staining (Forsyth et al. (2011) PLoS One 6:e28032). Furthermore, non-motor symptoms can precede PD diagnosis by several years or decades and persist as the disease progresses (Strang, R. R. (1965) Med. J. Aust., 1:842-843). In the context of these prodromes and Braak staging of Parkinson's disease neuropathology, the instant findings of chronic inflammation in the periphery strengthens the "dual hit" theory, which indicates that the etiology of PD may be infection by a pathogen that gains entry to the CNS through the periphery (e.g., nasal and gut tissues) (Hawkes et al. (2007) Neuropathol. Appl. Neurobiol., 33:599-614).

In summary, the instant data indicates that a chronic-inducer of T cell stimulation in the periphery exists in PD and provides an association between the adaptive immune system activity and motor dysfunction. Notably, it was observed that immunological markers of chronic T cell activation are associated with disease severity, but not age or duration of disease. As UPDRS-III scores (i.e., motor dysfunction) increase, the Tem cell phenotype, indicative of chronic activation, predominates. CD45RA expression decreases, while CD45RO expression increases; cell surface expression of α4β7 and CD31 decline, while FAS expression increases, and CD27 transcription levels decrease. The decrease in CD31 in combination with increased FAS, contributes to apoptosis and the subsequent relative lymphopenia. In addition, the decrease in CD31 on Treg in PD patients with more severe motor dysfunction, may contribute to impaired suppressive function at lower Treg:Tresp ratios. Altogether, these data combined with recent reports of increased intestinal permeability and the presence of modified α-Syn, Lewy body and infectious inflammatory mediators in the PD gut tissue, lend support to the "dual hit" theory whereby peripheral engagement of antigens such as modified-self α-Syn affect disease progression.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of diagnosing and treating Parkinson's disease in a subject said method comprising:
   detecting in a biological sample obtained from said subject markers from the C—X—C chemokine receptor type 4 (CXCR-4) or phosphatidylinositol 3-kinase regulatory subunit 1 (alpha) (PIK3R1) signaling pathways,
   measuring the amount of said markers in said biological sample with an antibody immunologically specific for each marker, and
   determining the presence and severity of Parkinson's disease in said subject by comparing the amount of said markers in said biological sample with the amount of said marker in a biological sample from a healthy control and/or the amount of said markers in a biological sample from a subject with Parkinson's disease,
   wherein said markers include CD4, CD127, and CD25,
   wherein a modulation in the amount of said markers indicating an increase in effector memory T cells (Tem) in said subject compared to healthy individuals indicates Parkinson's disease in said subject and wherein the increase in effector memory T cells (Tem) in said subject directly correlates with the severity of Parkinson's disease,
   said method further comprising administering a therapeutic regimen to the subject upon a diagnosis of Parkinson's disease based on an increase in effector memory T cells (Tem) as determined by comparing the amount of said markers in said biological sample with the amount of said marker in a biological sample from a healthy control and/or the amount of said markers in a biological sample from a subject with Parkinson's disease,
   wherein said treatment regimen is selected from the group consisting of dopamine replacement therapy, a Parkinson's disease vaccine, deep brain stimulation, and granulocyte/macrophage-colony stimulating factor (GM-CSF).

2. The method of claim 1, wherein said treatment regimen is dopamine replacement therapy.

3. The method of claim 1, wherein said markers further include at least one marker selected from the group consisting of PIK3R1, CXCR4, integrin alpha-V (ITGAV), integrin alpha-E (ITGAE), integrin beta-7 (ITGB7), integrin alpha-4 (ITGA4), cluster of differentiation (CD31), secreted phosphoprotein 1 (SPP1), cluster of differentiation 45 (CD45), forkhead box P3 (FoxP3), fibronectin 1 (FN1), CD27, and FAS.

4. The method of claim 1, wherein said markers further include at least one marker selected from the group consisting of CD45RA, CD45RO, CD31, FAS, CD27, integrin beta-7, and integrin alpha-4.

5. The method of claim 1, wherein said markers further include at least one marker selected from the group consisting of CD45RA, CD45RO, CD31, FAS, integrin beta-7, and integrin alpha-4.

6. The method of claim 1, wherein said biological sample is blood.

7. The method of claim 1, wherein said CD4, CD127, and CD25 are the only markers detected and measured.

8. The method of claim 1, wherein the measuring of the amount of said marker comprises performing an ELISA with said antibody immunologically specific for said marker.

9. The method of claim 1, wherein the measuring of the amount of said marker comprises performing flow cytometry with said antibody immunologically specific for said marker.

10. The method of claim 1, wherein said effector memory T cells (Tem) are positive for CD4, CD127, and CD25.

11. The method of claim 1, wherein said effector memory T cells (Tem) are positive for CD4, CD127, CD25, and CD45RO.

12. The method of claim 1, wherein said antibody immunologically specific for said marker is conjugated to a detectable agent.

13. The method of claim 12, wherein said detectable agent is a fluorescent agent.

14. The method of claim 1, wherein said severity of Parkinson's disease is provided in terms of Unified Parkinson's Disease Rating Scale (UPDRS) III scores.

15. The method of claim 14, wherein the increase in effector memory T cells (Tem) in said subject indicates the subject has a UPDRS-III score of 30 or higher.

16. A method of diagnosing and treating Parkinson's disease in a subject said method comprising:
   a) measuring the amount in a biological sample obtained from said subject markers from the C—X—C chemokine receptor type 4 (CXCR-4) or phosphatidylinositol 3-kinase regulatory subunit 1 (alpha) (PIK3R1) signaling pathways, wherein said markers include CD4, CD127, and CD25, and wherein the amount of said markers in said biological sample is measured with an antibody immunologically specific for each marker;
   b) comparing the amount of effector memory T cells (Tem) in said subject based on the amount of said markers in said biological sample from step a) with the amount of effector memory T cells (Tem) in a biological sample from a healthy control based on the amount of said markers;
   c) determining the presence and severity of Parkinson's disease in said subject based on the comparison of the amount of effector memory T cells (Tem) in said subject and the amount of effector memory T cells (Tem) from a healthy control in step b), wherein an increase in effector memory T cells (Tem) in said subject compared to healthy individuals indicates Parkinson's disease in said subject, and wherein the increase in effector memory T cells (Tem) in said subject directly correlates with the severity of Parkinson's disease; and
   d) administering a therapeutic regimen to the subject upon a diagnosis of Parkinson's disease in step c), wherein said treatment regimen is selected from the group consisting of dopamine replacement therapy, a Parkinson's disease vaccine, deep brain stimulation, and granulocyte/macrophage-colony stimulating factor (GM-CSF).

17. The method of claim 16, wherein step c) comprises determining that the subject has a Unified Parkinson's Disease Rating Scale (UPDRS) III score of 30 or higher based on the increase in effector memory T cells (Tem) in said subject.

* * * * *